(12) United States Patent
Greenan et al.

(10) Patent No.: US 11,672,661 B2
(45) Date of Patent: Jun. 13, 2023

(54) ANNULOPLASTY SYSTEMS AND METHODS

(71) Applicant: Silara Medtech Inc., Santa Rosa, CA (US)

(72) Inventors: Trevor M. Greenan, Santa Rosa, CA (US); Mathew A. Haggard, Santa Rosa, CA (US); Do D. Uong, Santa Rosa, CA (US); Leonardo R. Rodriguez, Santa Rosa, CA (US); Clara Brechtel, Santa Rosa, CA (US)

(73) Assignee: Silara Medtech Inc., Santa Rosa, CA (US)

( * ) Notice: Subject to any disclaimer, the term of this patent is extended or adjusted under 35 U.S.C. 154(b) by 0 days.

(21) Appl. No.: 16/548,543

(22) Filed: Aug. 22, 2019

(65) Prior Publication Data

US 2021/0052387 A1 Feb. 25, 2021

(51) Int. Cl.
*A61F 2/24* (2006.01)

(52) U.S. Cl.
CPC .......... *A61F 2/2457* (2013.01); *A61F 2/2445* (2013.01); *A61F 2/2466* (2013.01); *A61F 2220/0016* (2013.01); *A61F 2220/0091* (2013.01)

(58) Field of Classification Search
CPC ..... A61F 2/2442; A61F 2/2445; A61F 2/2448
See application file for complete search history.

(56) References Cited

U.S. PATENT DOCUMENTS

| | | | |
|---|---|---|---|
| 5,868,779 A | 2/1999 | Ruiz | |
| 5,895,404 A | 4/1999 | Ruiz | |
| 5,928,261 A | 7/1999 | Ruiz | |
| 5,935,112 A | 8/1999 | Stevens et al. | |
| 5,954,765 A | 9/1999 | Ruiz | |
| 6,261,273 B1 | 7/2001 | Ruiz | |
| 6,702,826 B2 | 3/2004 | Liddicoat et al. | |
| 6,860,463 B2 | 3/2005 | Hartley | |
| 6,942,694 B2 | 9/2005 | Liddicoat et al. | |
| 6,986,775 B2 | 1/2006 | Morales et al. | |
| 7,166,127 B2 | 1/2007 | Spence et al. | |
| 7,297,150 B2 | 11/2007 | Cartledge et al. | |
| 7,338,518 B2 | 3/2008 | Chobotov | |

(Continued)

FOREIGN PATENT DOCUMENTS

WO WO2013/155970 A1 10/2013
WO WO2016/150260 A1 9/2016

(Continued)

*Primary Examiner* — Leslie Lopez

(74) *Attorney, Agent, or Firm* — Shay Glenn LLP

(57) ABSTRACT

An exemplary method of performing an annuloplasty procedure includes introducing a catheter into a left atrium of a heart, deploying a first member from the catheter, anchoring the first member to a posterior side of a mitral valve annulus in the left atrium, deploying a second member from the catheter, anchoring the second member to an anterior side of the mitral valve annulus in the left atrium, deploying a flexible tensile member from the catheter, attaching the tensile member to both the first member and the second member and applying tension to the tensile member to draw the first member and the second member toward one another and bring the posterior side and the anterior side of the mitral valve annulus into closer approximation. Annuloplasty systems and components are also disclosed.

17 Claims, 29 Drawing Sheets

(56) References Cited

U.S. PATENT DOCUMENTS

| | | |
|---|---|---|
| 7,588,582 B2 | 9/2009 | Starksen et al. |
| 7,753,924 B2 | 7/2010 | Starksen et al. |
| 7,892,275 B2 | 2/2011 | Hartley et al. |
| 8,202,315 B2 | 6/2012 | Hlavka et al. |
| 8,241,351 B2 | 8/2012 | Cabiri |
| 8,277,502 B2 | 10/2012 | Miller et al. |
| 8,512,401 B2 | 8/2013 | Murrary et al. |
| 8,518,107 B2 | 8/2013 | Tsukashima et al. |
| 8,864,822 B2 | 10/2014 | Spence et al. |
| 8,911,494 B2 | 12/2014 | Hammer et al. |
| 8,926,697 B2 | 1/2015 | Gross et al. |
| 8,945,059 B2 | 2/2015 | Loewen |
| 9,011,520 B2 | 4/2015 | Miller et al. |
| 9,180,005 B1 | 11/2015 | Lashinski et al. |
| 9,192,471 B2 | 11/2015 | Bolling |
| 9,216,277 B2 | 12/2015 | Myers |
| 9,446,018 B2 | 9/2016 | Su et al. |
| 9,492,276 B2 | 11/2016 | Lee et al. |
| 9,713,530 B2 | 7/2017 | Cabiri et al. |
| 9,895,222 B2 | 2/2018 | Zeng et al. |
| 10,251,763 B2 | 4/2019 | Wang |
| 10,463,483 B2 | 11/2019 | Lim et al. |
| 10,687,932 B2 | 6/2020 | Zi et al. |
| 2003/0225379 A1 | 12/2003 | Schaffer et al. |
| 2007/0049942 A1 | 3/2007 | Hindrichs et al. |
| 2009/0008883 A1 | 4/2009 | Bishop et al. |
| 2009/0093670 A1 | 4/2009 | Annest et al. |
| 2011/0166649 A1* | 7/2011 | Gross .................... A61F 2/2445 623/2.36 |
| 2012/0245604 A1 | 9/2012 | Tegzes |
| 2012/0296407 A1 | 11/2012 | Caselnova |
| 2014/0052232 A1 | 2/2014 | Cragg et al. |
| 2015/0018941 A1 | 1/2015 | Lee et al. |
| 2016/0045311 A1 | 2/2016 | McCann et al. |
| 2016/0120645 A1 | 5/2016 | Alon |
| 2016/0213919 A1 | 7/2016 | Suwito et al. |
| 2017/0056171 A1 | 3/2017 | Cooper et al. |
| 2017/0165068 A1 | 6/2017 | Machold et al. |
| 2017/0189187 A1 | 7/2017 | Ruiz et al. |
| 2017/0340443 A1 | 11/2017 | Sterns et al. |
| 2018/0311039 A1 | 11/2018 | Cohen et al. |
| 2018/0318080 A1 | 11/2018 | Quill et al. |
| 2019/0125325 A1 | 5/2019 | Sheps et al. |
| 2020/0230371 A1 | 7/2020 | Klausen et al. |
| 2021/0030540 A1 | 2/2021 | Marchand et al. |
| 2021/0275306 A1 | 9/2021 | Greenan et al. |

FOREIGN PATENT DOCUMENTS

| | | |
|---|---|---|
| WO | WO2016/150261 A1 | 9/2016 |
| WO | WO2019/105073 A1 | 6/2019 |
| WO | WO2019/116322 A1 | 6/2019 |
| WO | WO2019/179447 A1 | 9/2019 |
| WO | WO2020/134052 A1 | 7/2020 |
| WO | WO2020/134053 A1 | 7/2020 |
| WO | WO2021/034789 A1 | 2/2021 |

* cited by examiner

ANNULOPLASTY SYSTEMS AND METHODS

INCORPORATION BY REFERENCE

All publications and patent applications mentioned in this specification are herein incorporated by reference for all intents and purposes to the same extent as if each individual publication or patent application was specifically and individually indicated to be incorporated by reference.

FIELD

Embodiments of the disclosure relate generally to implanted medical devices. Specifically, some implementations of the present invention relate to apparatus and methods for repairing a mitral valve.

BACKGROUND

The mitral valve is located at the junction between the left atrium and the left ventricle of the heart. During diastole, the valve opens, in order to allow the flow of blood from the left atrium to the left ventricle. During systole, when the left ventricle pumps blood into the body via the aorta, the valve closes to prevent the backflow of blood into the left atrium. The mitral valve is composed of two leaflets (the posterior leaflet and the anterior leaflet), which are located at the mitral annulus, the annulus being a ring that forms the junction between the left atrium and the left ventricle. The mitral valve leaflets are tethered to papillary muscles of the left ventricle via chordae tendineae. The chordae tendineae prevent the mitral valve leaflets from averting into the left atrium during systole.

Mitral valve regurgitation is a condition in which the mitral valve does not close completely, resulting in the backflow of blood from the left ventricle to the left atrium. In some cases, regurgitation is caused by dilation of the mitral annulus, and, in particular, by an increase in the anteroposterior diameter of the mitral annulus. Alternatively or additionally, mitral regurgitation is causes by dilation of the left ventricle that, for example, may result from an infarction. The dilation of the left ventricle results in the papillary muscles consistently tethering the mitral valve leaflets into an open configuration, via the chordae tendineae.

Prior art methods and devices exist for treating mitral regurgitation. They involve either replacing or repairing the mitral valve. Replacing the valve is typically done either transapically or transseptally. Repairing the valve typically falls into one of four categories: leaflet clip; direct annuloplasty; indirect annuloplasty or chordae repair. Direct and indirect annuloplasty both involve reshaping the mitral annulus and or the left ventricle of a subject so that the anterior and posterior leaflet coapt properly. For some annuloplasty applications, a ring is implanted in the vicinity of (e.g., on or posterior to) the mitral annulus. The purpose of the ring is to reduce the circumference of the mitral annulus.

In light of the above prior art, it is desirable to provide improved systems and methods for treating mitral valve regurgitation.

SUMMARY

According to aspects of the disclosure, systems and methods for performing an annuloplasty procedure are provided. In some embodiments, a method includes introducing a catheter into a left atrium of a heart, deploying a first member from the catheter, anchoring the first member to a posterior side of a mitral valve annulus in the left atrium, deploying a second member from the catheter, anchoring the second member to an anterior side of the mitral valve annulus in the left atrium, deploying a flexible tensile member from the catheter, attaching the tensile member to both the first member and the second member and applying tension to the tensile member to draw the first member and the second member toward one another and bring the posterior side and the anterior side of the mitral valve annulus into closer approximation.

In some embodiments, a method of performing an annuloplasty procedure includes the steps of introducing a catheter into a left atrium of a heart and deploying a first member from the catheter. The first member is anchored to a posterior side of a mitral valve annulus in the left atrium. A second member is deployed from the catheter and anchored to an anterior side of the mitral valve annulus in the left atrium. A flexible tensile member is deployed from the catheter and attached to both the first member and the second member. Tension is applied to the tensile member to draw the first member and the second member toward one another and bring the posterior side and the anterior side of the mitral valve annulus into closer approximation.

In some embodiments, the second member is deployed and anchored separately from the first member. The step of anchoring the first member may include attaching at least two separate anchors by screwing them into the annulus. The method may further include deploying a separate third member from the catheter, anchoring the third member to an anterior side of the mitral valve annulus in the left atrium, attaching a tensile member to both the first member and the third member, and applying tension to the tensile member attached between the first member and the third member to bring the posterior side and the anterior side of the mitral valve annulus into closer approximation. In some embodiments, the third member is deployed and anchored separately from the first member and the second member. The tensile member attached between the first member and the second member, and the tensile member attached between the first member and the third member, may be two separate tensile members. In some embodiments, tension is applied independently to the two separate tensile members.

In some embodiments, the second member is anchored toward a lateral side of the mitral valve annulus and the third member is anchored toward a medial side of the mitral valve annulus. The second member may have at least one anchor within proximity of the lateral trigon and the third member may have at least one anchor within proximity of the medial trigon. In some embodiments, at least one of the steps of anchoring the second member and the third member comprises attaching at least two separate anchors by screwing the separate anchors into the annulus. In some embodiments, a dimensional reduction of the mitral valve annulus in an anterior-posterior direction can be different on the lateral side and the medial side.

In some embodiments, the tensile member is not attached to either the first member or the second member until it is being deployed from the catheter in vivo. In some embodiments, the separate tensile members are not attached to any of the first member, the second member or the third member until they are being deployed from the catheter in vivo. At least one of the first member and the second member may have the tensile member pre-attached prior to the first member or the second member being deployed from the catheter. In some embodiments, the first member includes an extended feature configured to engage the tensile member.

In some embodiments, the second member includes an extended feature configured to engage the tensile member. The step of deploying a flexible tensile member from the catheter may include snaring the first member and the second member one at a time with the tensile member. In some embodiments, the first member has an elongated shape, and the method further includes rotating the elongated first member into a desired position before anchoring it to the posterior side of a mitral valve annulus. The elongated first member may have more than one lead attached to it during the rotating step.

In some embodiments, an annuloplasty system includes a first member, at least one first member anchor, a second member, at least one second member anchor, and a first flexible tensile member. The at least one first member anchor is configured to anchor the first member to a posterior side of a mitral valve annulus in a left atrium of a heart. The at least one second member anchor is configured to anchor the second member to an anterior side of the mitral valve annulus in the left atrium. The first flexible tensile member is configured to span between the first member and the second member such that tension may be applied to the first tensile member to draw the first member and the second member toward one another and bring the posterior side and the anterior side of the mitral valve annulus into closer approximation. All of the elements of the annuloplasty system are configured to be deployed into the left atrium through a catheter.

In some embodiments, the first member is elongated and capable of taking on a curved shape. The first member may include a series of slits that allows the first member to flex. In some embodiments, the annuloplasty system further includes a third member and at least one third member anchor configured to anchor the third member to the anterior side of the mitral valve annulus in the left atrium. The annuloplasty system may further include a second flexible tensile member configured to span between the first member and the third member such that tension may be applied to the second tensile member to draw the first member and the third member toward one another and bring the posterior side and the anterior side of the mitral valve annulus into closer approximation. In some embodiments, the first member includes at least two extended features, each configured to engage either the first tensile member or the second tensile member.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION

Figure 1:
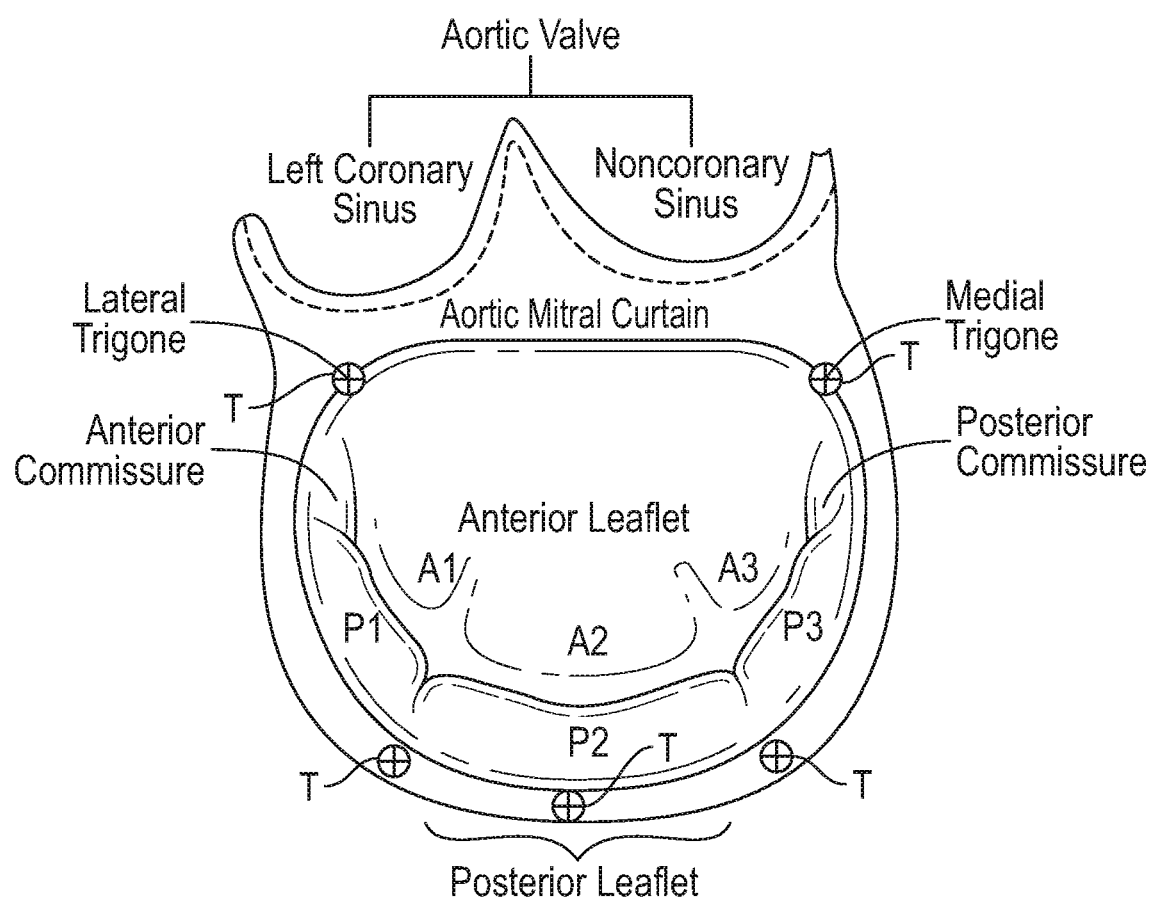
FIG. 1 is a generally cranial to caudal view showing aspects of a human mitral valve.

Referring to FIG. 1, elements of a mitral valve are shown. In particular, the mitral valve comprises an anterior leaflet, a posterior leaflet, an anterior-lateral commissure, a posterior-medial commissure, a lateral trigone (sometimes referred to as left) and a medial trigone (sometimes referred to as right). The anterior leaflet includes three divisions A1, A2 and A3. Similarly, the posterior leaflet also includes three divisions P1, P2 and P3. According to aspects of the present disclosure, in some implementations device anchors may be placed at or near each of the target locations T as shown.

Figure 2:
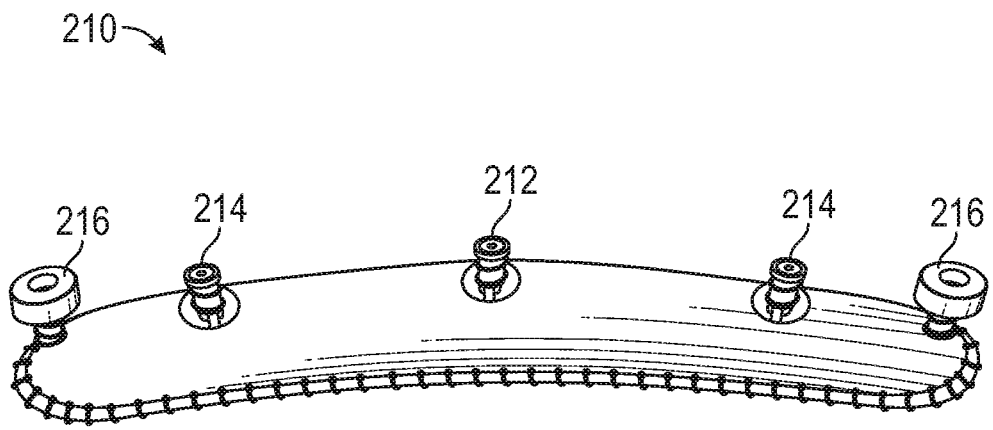
FIG. 2 is a perspective view showing an exemplary posterior bar constructed according to aspects of the present disclosure.

Referring to FIG. 2, an exemplary posterior bar 210 constructed according to aspects of the present disclosure is shown. Posterior bar 210 is configured to be implanted in the left atrium on or near the mitral annulus adjacent to the posterior leaflet, as will be subsequently described in more detail. As such, in this exemplary embodiment, posterior bar 210 is an elongated tubular structure that is curved to match the anatomy of the mitral annulus in this location. Posterior bar 210 may be provided with a low profile as shown to minimize the amount of irregular structure in the atrium that might be a potential site for thrombosis. In this exemplary embodiment, posterior bar 210 is provided with atraumatic edges to limit the potential for tissue damage, and is covered in polyethylene terephthalate (PET) fabric to aid with tissue ingrowth.

In this exemplary embodiment, posterior bar 210 is provided with a middle tissue anchor guide 212 and two end tissue anchor guides 214. In some embodiments, middle tissue anchor guide 212 is identical to end tissue anchor guides 214, and in other embodiments it is configured differently, such as having features that facilitate the steering/torqueing of posterior bar 210 during delivery. In some embodiments, as will be subsequently described herein, there may be no middle tissue anchor guide, and there may be greater or fewer than the three tissue anchor guides provided in this exemplary embodiment. Anchor guides 212 and 214 may be configured to pivot relative to posterior bar 210 such that they can move from a retracted state and a deployed state. In the retracted state, anchor guides 212 and 214 may extend generally parallel to bar 210 so that they and bar 210 may together pass through a lumen of a catheter. In the deployed state, anchor guides 212 and 214 may extend generally perpendicular to bar 210 as shown in FIG. 2 so that they may be used to thread a tissue anchor over the guide, through apertures in bar 210 and into adjoining tissue to secure bar 210 to the tissue.

One or more snare features 216 may be provided on posterior bar 210. In this exemplary embodiment, two snare features 216 are provided, one near each end of posterior bar 210. Snare feature 216 may be configured to prominently extend from posterior bar 210 such that they can easily engage with one or more tensile members/snares, and also to prevent the tensile members from disengaging during manipulation. In some embodiments, snare features 216 are configured to be easily imaged under fluoroscopy and echocardiography to aid in positioning posterior bar 210 during delivery and attachment to tissue, and to aid in connecting tensile members to the snare features 216.

Posterior bar 210 may be designed to preferentially load anchors in shear versus tension with respect to the anatomy. Torque control features may be provided to allow the initial positioning of posterior bar 210, and to allow the ability to move the implant as subsequent anchors are delivered to match the anatomy.

Posterior bar 210 may also be provided with some level of flexibility to allow for in vivo adjustment of the bar to contour to the particular subject's anatomy. The flexibility of posterior bar 210 may also serve to allow the bar to flex during the cardiac cycle. In some embodiments, the flexibility of posterior bar 210 is created by providing a series of slits (not shown in FIG. 1) transverse to the longitudinal axis of the bar. In some embodiments, the slits and or other flexibility-providing features may be configured to limit the minimum radius of posterior bar 210 when implanted to ensure it applies a more uniform tension to the posterior side of the mitral annulus.

Figure 3:
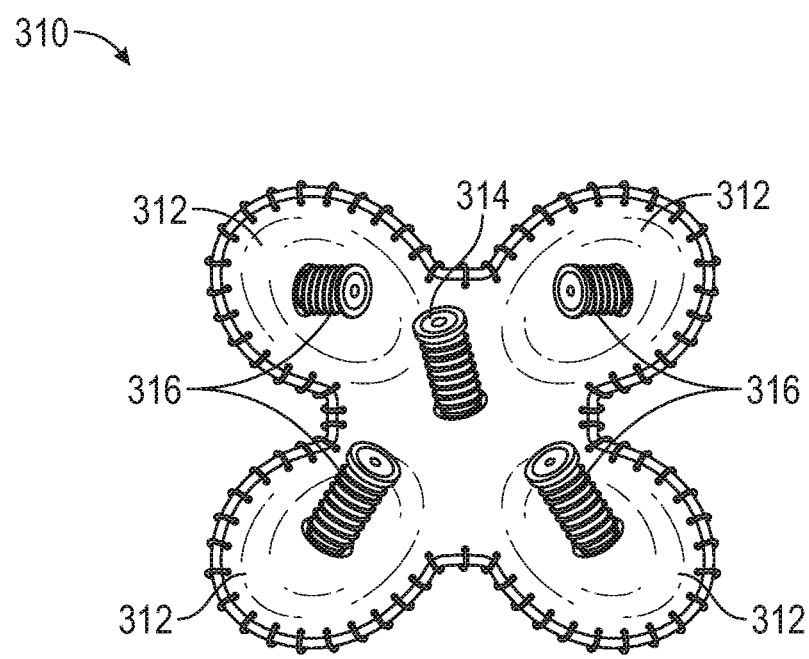
FIG. 3 is a top plan view showing an exemplary anterior pad constructed according to aspects of the present disclosure.

Referring to FIG. 3, an exemplary anterior pad 310 constructed according to aspects of the present disclosure is shown. Anterior pad 310 is configured to be implanted in the left atrium on or near the mitral annulus adjacent to the anterior leaflet, particularly on a trigone, as will be subsequently described in more detail. In this exemplary embodiment, anterior pad 310 is a generally flat structure provided with four petals 312 radially extending from a central portion. In other embodiments, more, fewer or no petals may be provided. A primary tissue anchor 314 may be located in the center of anterior pad 310. In some embodiments, additional tissue anchors 316 may be provided, such as an additional anchor 316 near the center of each petal 312, as shown. In some embodiments, primary tissue anchor 314 is identical to additional tissue anchors 316, and in other embodiments it is configured differently, such as having features that facilitate the positioning of anterior pad 310 during delivery. The petals 312 may be designed to fold into a compact configuration such that anterior pad 310 may be delivered through a catheter.

Anterior pad 310 may be provided with a low profile as shown to minimize the amount of irregular structure in the atrium that might be a potential site for thrombosis. In this exemplary embodiment, anterior pad 310 is provided with atraumatic edges to limit the potential for tissue damage, and is covered in polyethylene terephthalate (PET) fabric to aid with tissue ingrowth.

One or more snare features may be provided on anterior pad 310. In this exemplary embodiment, the top ends of tissue anchors 314 and 316 are configured to engage with one or more tensile members/snares These snare features may be configured to prominently extend from anterior pad 310 such that they can easily engage with one or more tensile members/snares, and also to prevent the tensile members from disengaging during manipulation. In some embodiments, the snare features and or the entire anterior pad 310 are configured to be easily imaged under fluoroscopy and echocardiography to aid in positioning anterior pad 310 during delivery and attachment to tissue, and to aid in connecting tensile members to the snare features. Anterior pad 310 may be designed to preferentially load anchors in shear versus tension with respect to the anatomy.

Figure 4:
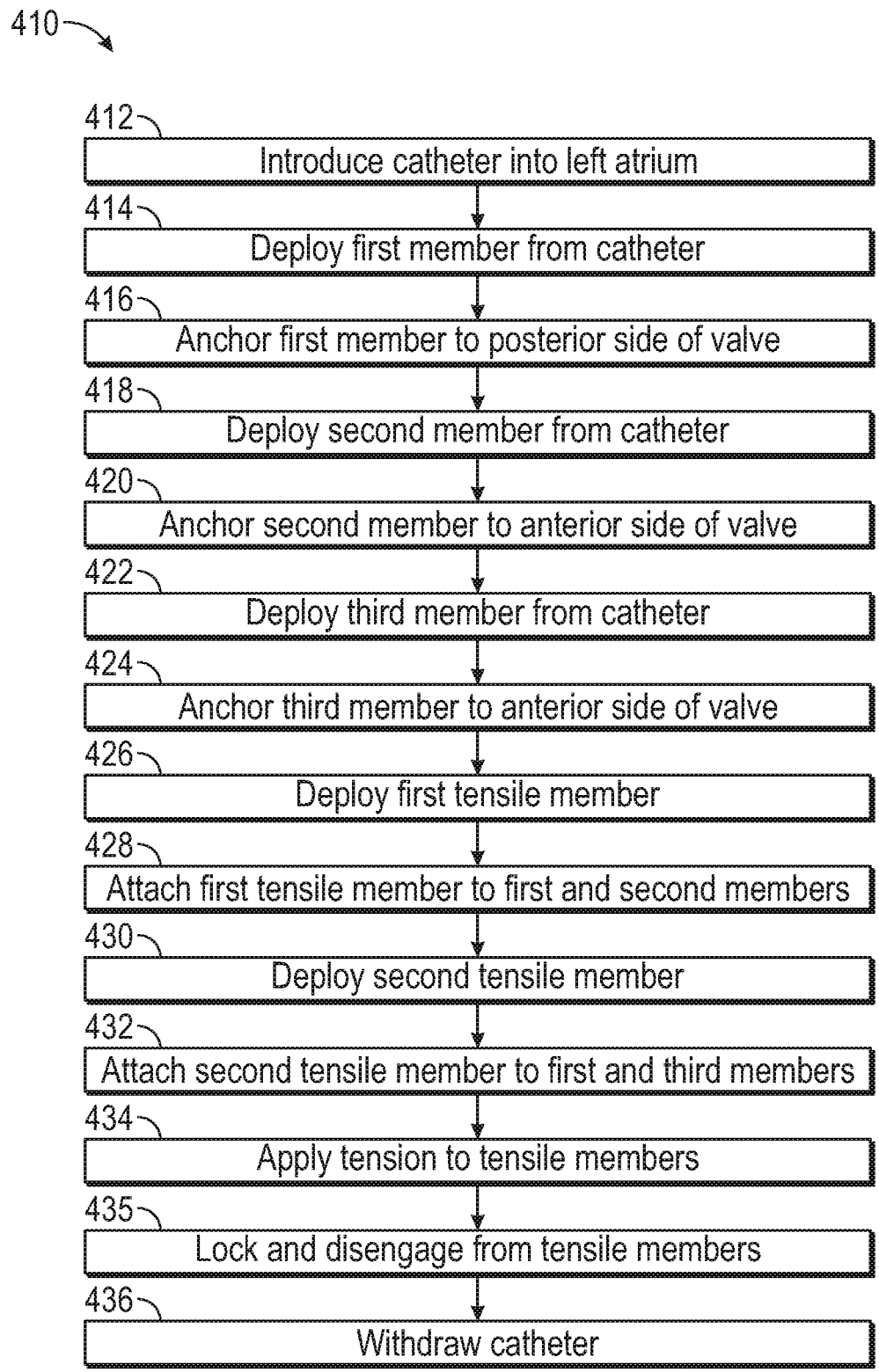
FIG. 4 is a flowchart schematically illustrating an exemplary method of performing an annuloplasty procedure according to aspects of the present disclosure.

Referring to FIG. 4, an exemplary method of performing an annuloplasty procedure according to aspects of the present disclosure is shown. The steps of this exemplary method 410 will be described in reference to the flowchart shown in FIG. 4 and the series of images shown in FIGS. 5-22. In each of the images shown in FIGS. 5-22, the view is looking in a generally caudal direction through the left atrium 510 toward the mitral valve 512 with the medial direction generally to the right. In some implementations of the method, one posterior bar 210 and one, two or more anterior pads 310 are implanted. In other implementations, different types or numbers of devices may be used. In FIGS. 5-22, posterior bar 210 is shown without a fabric cover for clarity. In this exemplary embodiment, at least one device anchor is placed at or near each of the five target locations T shown in FIG. 1.

In some implementations of method 410, the first step 412 of the method is introducing the distal end of a delivery catheter into the left atrium 510 of a subject. This may be performed using a transseptal approach, a left atrial approach or other methodology for gaining access to the left atrium. In the images shown in FIGS. 5-22, a transseptal approach is depicted with the distal end of catheter 514 passing through the septum 516 of the heart and into the left atrium 510 of the subject. In some implementations, an inner dilator (not shown) is located in the distal end of catheter 514 for crossing the septum.

Figure 5:
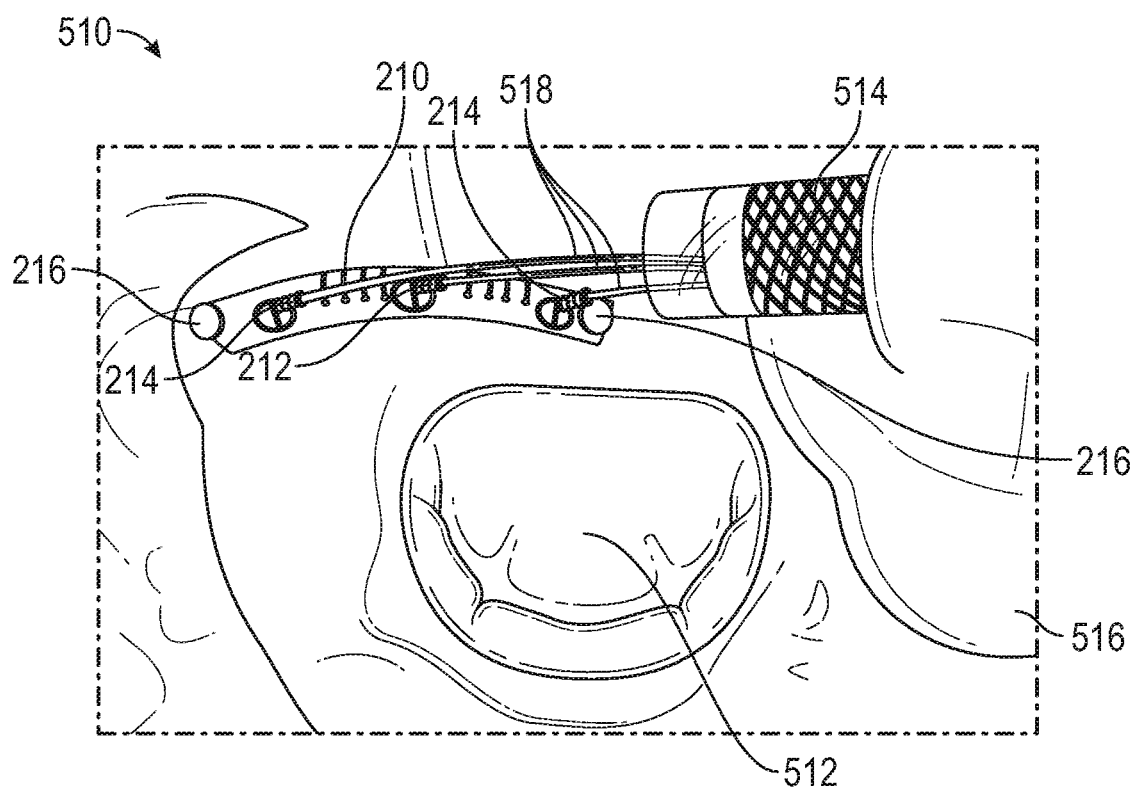
FIGS. 5-22 are a series of perspective views looking in a generally caudal direction through a left atrium at a mitral valve and showing the steps of the exemplary method outlined in FIG. 4.

Referring to FIGS. 4 and 5, once the distal end of catheter 514 is introduced into the left atrium 510, a posterior bar 210, sometimes referred to herein as a first member, may be deployed from the distal end of catheter 514 in step 414. In some implementations, catheter 514 is first introduced into the left atrium 510 before the posterior bar assembly is loaded into the proximal end of the catheter 514. In other implementations the posterior bar 210 along with its tissue anchor guides 212, 214 and snare features 216 may be pre-loaded into catheter (not shown) and advanced through catheter 514. As seen in FIG. 5, an anchor lead 518 may be removably attached to each of the tissue anchor guides 212 and 214 to push posterior bar 210 through catheter 514 and deploy it from the distal end.

Figure 6:
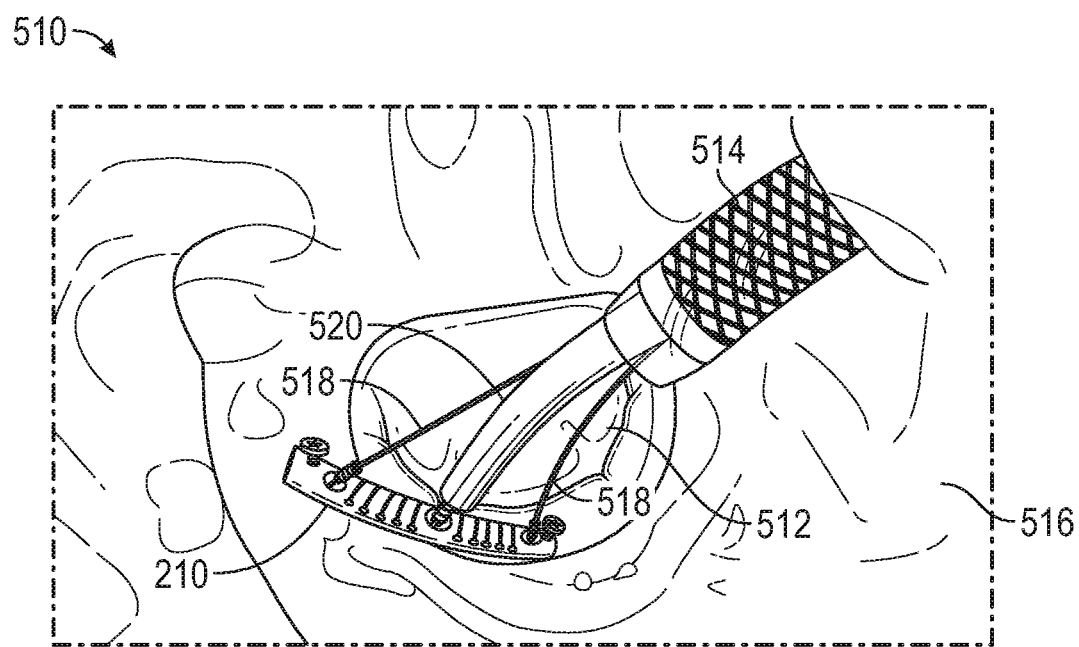
Figure 7:
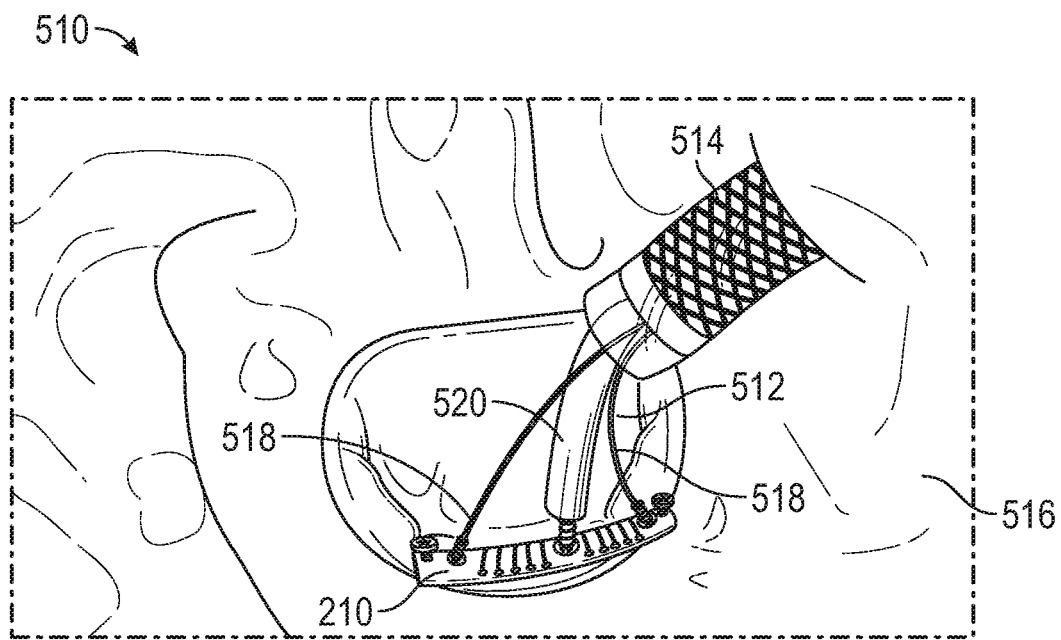

Referring to FIG. 6, once posterior bar 210 emerges from the distal end of catheter 514, a lead 518 attached to one of its ends may be pushed and the other pulled from the proximal end of catheter 514 to pivot posterior bar 210 into an orientation that is generally perpendicular to catheter 514, as shown. A steerable inner catheter 520 may be slid distally over middle lead 518 until features (such as recesses and/or castellations, not shown) engage with mating features on posterior bar 210 to keep bar 210 from rotating relative to inner catheter 520. Steerable inner catheter 520 may then be used to position and rotate posterior bar 210 until it is steered into its desired implantation location and orientation, as shown in FIG. 7. In some implementations, a torque driver coaxially located between lead 518 and steerable inner catheter 520 may be used to impart torque to posterior bar 210. Such an implementation is subsequently described in relation to FIGS. 40-46.

Figure 8:
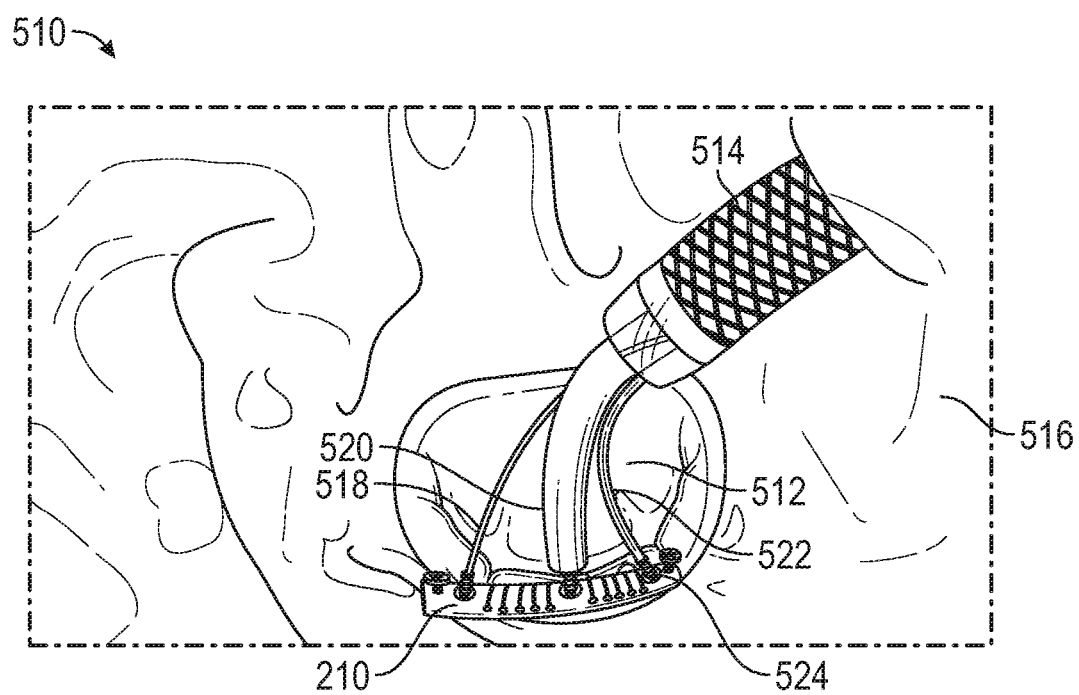
Figure 9:
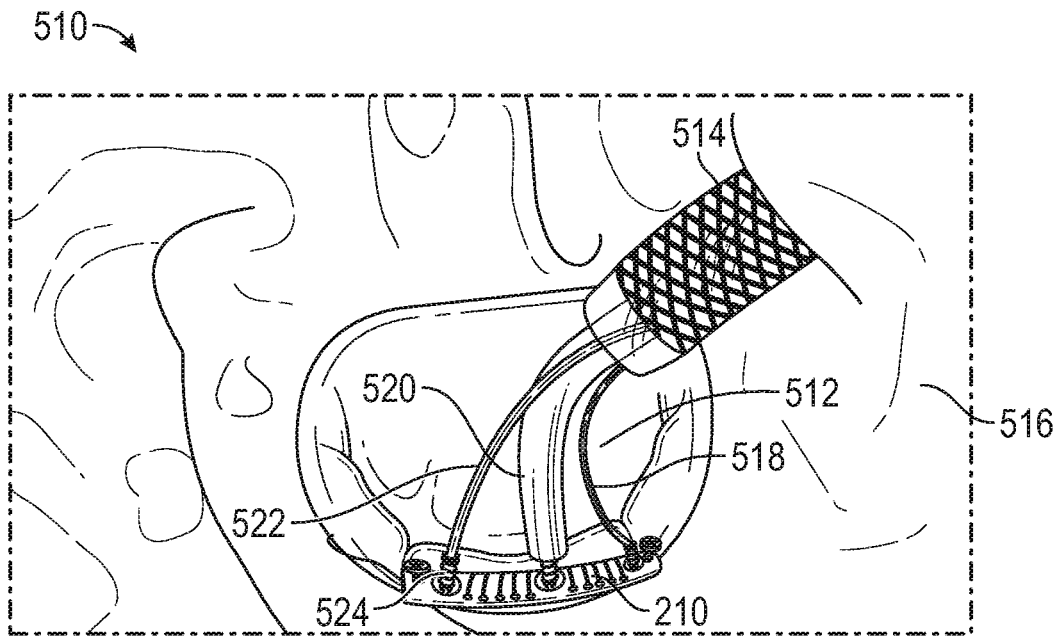
Figure 10:
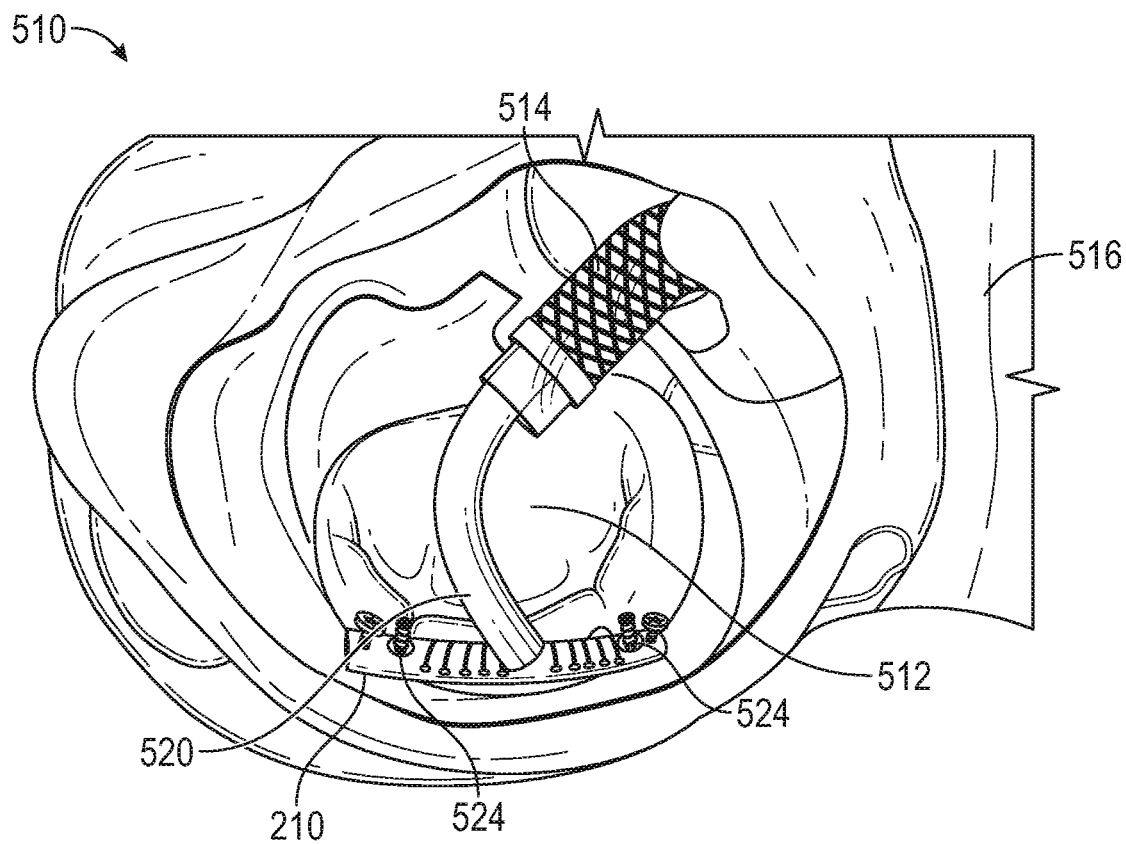
Figure 11:
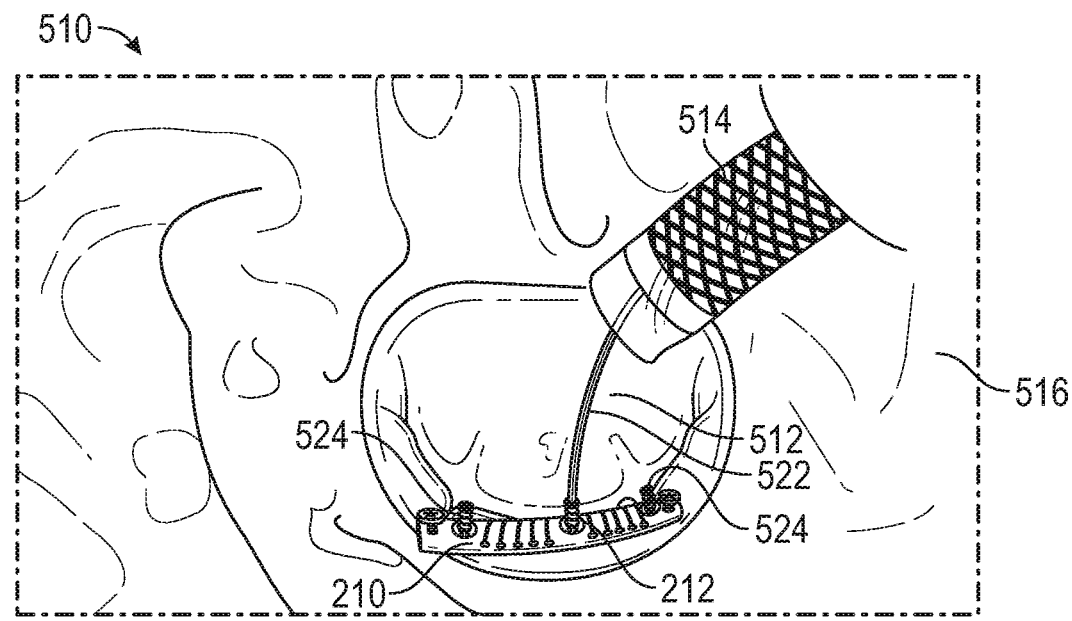

Referring to FIGS. 4 and 8-11, step 416 of exemplary method 410 will be described. In this step, posterior bar 210 (i.e. the first member) is anchored to the posterior side of mitral valve 512. This may be accomplished by first sliding a drive tube 522 with a helical tissue anchor 524 located on its distal end over lead 518 attached to the tissue anchor guide 214 located near the medial end of posterior bar 210, as shown in FIG. 8. While steerable inner catheter 520 holds posterior bar 210 against the mitral valve annulus tissue, drive tube 522 may be rotated to screw medial anchor 522 through posterior bar 210 and into the underlying tissue, as seen in FIG. 9. Drive tube 522 may then be removed from the medial anchor 214 and it (or another drive tube 522 with another helical tissue anchor 524) may be slid over lead 518 attached to the tissue anchor guide 214 located near the lateral end of posterior bar 210, as shown in FIG. 9. While medial anchor 524 and steerable inner catheter 520 (and in some implementations a torque driver inside catheter 520) hold posterior bar 210 against the mitral valve annulus tissue, drive tube 522 may be rotated to screw lateral tissue anchor 524 through bar 210 and into the underlying tissue, as seen in FIG. 10. Drive tube 522 may then be removed from the lateral anchor 524 and it (or another drive tube 522 with another helical tissue anchor 524) may be slid over lead 518 attached to the middle tissue anchor guide 212, as shown in FIG. 11. In some implementations, steerable inner catheter 520 may remain in place against posterior bar 210 when the center anchor is being placed (as shown in FIG. 10), or it may be removed from posterior bar 210 prior to drive tube 522 and middle anchor 524 being slid into engagement over middle tissue anchor guide 212 (as shown in FIG. 11.) While medial and lateral anchors 524 hold posterior bar 210 against the mitral valve annulus tissue, drive tube 522 may be rotated to screw middle anchor 524 through bar 210 and into the underlying tissue. FIGS. 10 and 11 show posterior bar 210 with the leads removed from the end tissue anchor guides, such as by unthreading.

Figure 12:
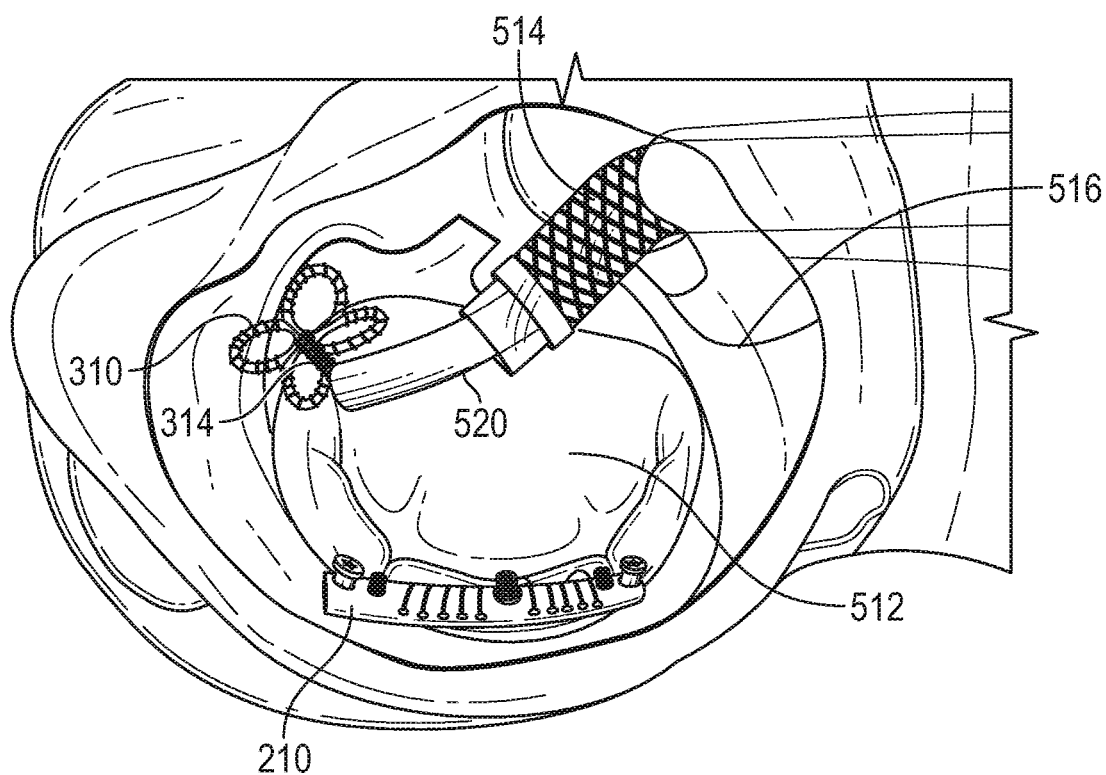

In step 416, it should be noted that after the initial anchor has been placed, torque control of the implant 210 provided by steerable inner catheter 520 (or in some implementations a torque driver located within catheter 520) can be used to guide the placement of subsequent anchors to implant 210. This eliminates the need for unguided anchor placement after the initial anchor has been placed. FIG. 12 shows posterior bar 210 with the three anchors placed and all leads removed.

Referring to FIGS. 4 and 12, step 418 of exemplary method 410 will be described. In this step, anterior pad 310 (sometimes referred to herein as a second member) is deployed from the distal end of catheter 514. In some implementations, anterior pad 310 is steered toward the lateral trigone with steerable inner catheter 520 as shown in FIG. 12. (The lateral trigone is also shown in FIG. 1.)

Figure 13:
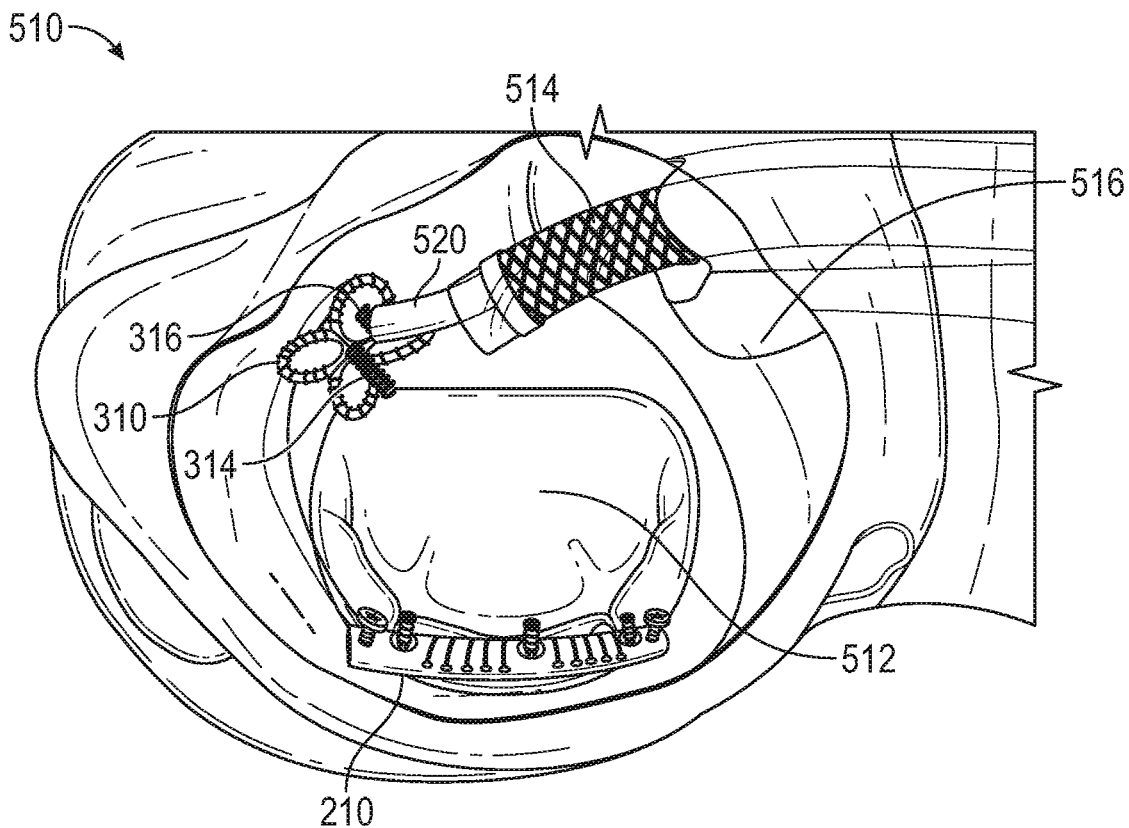

Referring to FIGS. 4, 12 and 13, step 420 of exemplary method 410 will be described. In this step, anterior pad 310 (sometimes referred to herein as a second member) is anchored to the anterior side of mitral valve 512. In some implementations, anterior pad 310 is anchored to the lateral trigone as shown with a single anchor 314. A drive tube (not shown) may be used within steerable inner catheter 520 to screw anchor 314 into place. As shown in FIG. 13, additional anchor(s) 316 may be used to further secure anterior pad 310 to the lateral trigone.

In step 420, it should be noted that after the initial anchor has been placed, its lead can remain in place through steerable inner catheter 520 such that the lead and catheter 520 can be used to guide the placement of subsequent anchors to implant 310. This eliminates the need for unguided anchor placement after the initial anchor has been placed.

Figure 14:
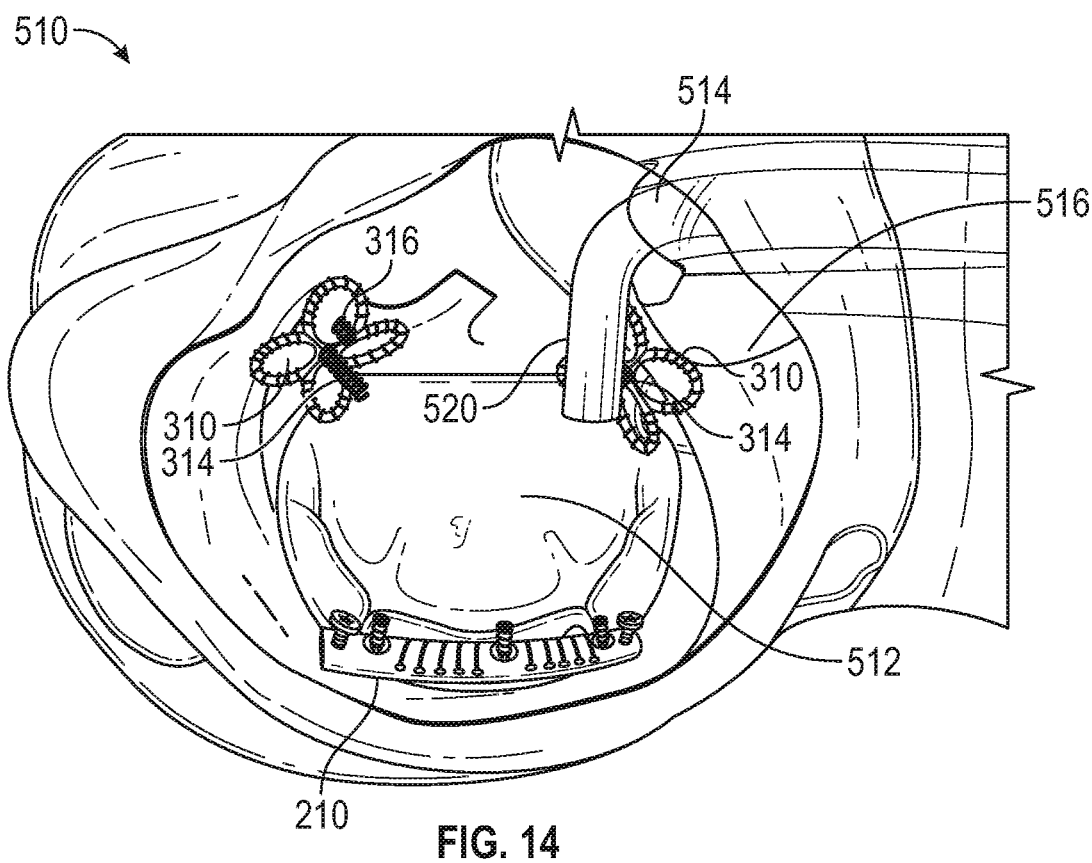

Referring to FIGS. 4 and 14, steps 422 and 424 of exemplary method 410 will be described. In these steps, another anterior pad 310 (sometimes referred to herein as a third member) is deployed from the distal end of catheter 514. In some implementations, anterior pad 310 is steered toward the medial trigone with steerable inner catheter 520 as shown in FIG. 14. (The medial trigone is also shown in FIG. 1.) Anterior pad 310 may then anchored to the anterior side of mitral valve 512. In some implementations, anterior pad 310 is anchored to the medial trigone as shown with a single anchor 314. A drive tube (not shown) may be used within steerable inner catheter 520 to screw anchor 314 into place. As with the lateral anterior pad 310, additional anchor(s) may be used to further secure the medial anterior pad 310 to the medial trigone.

In step 424, it should be noted that after the initial anchor has been placed, its lead can remain in place through steerable inner catheter 520 such that the lead and catheter 520 can be used to guide the placement of subsequent anchors to implant 310. This eliminates the need for unguided anchor placement after the initial anchor has been placed.

Figure 15:
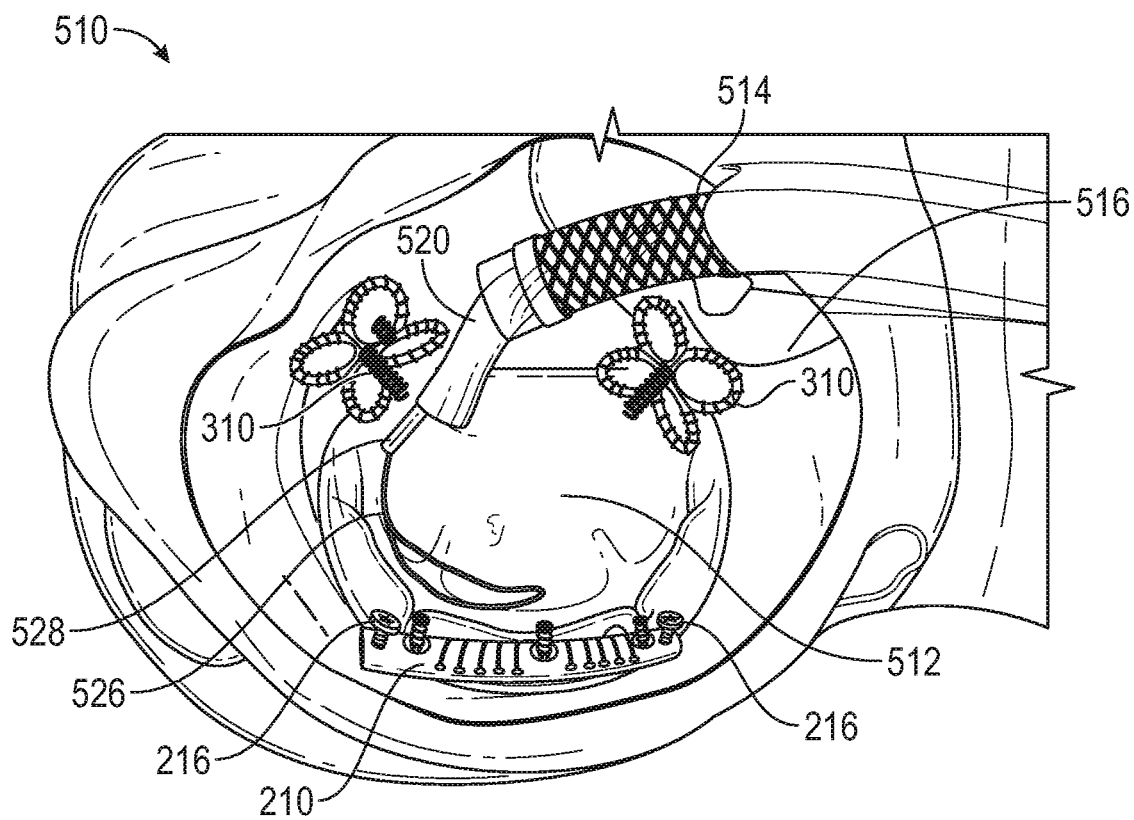

Referring to FIGS. 4 and 15, step 426 of exemplary method 410 will be described. In this step, a first tensile member or snare 526 is deployed from the distal end of catheter 514 through steerable inner catheter 520 as shown. A snare sheath 528 may be used to direct the first tensile member 526 toward implant features. Snare sheath 528 may also be used to tighten first tensile member 526 around the implant features by pulling proximally on the tensile member 526 relative to the sheath 528.

Figure 16:
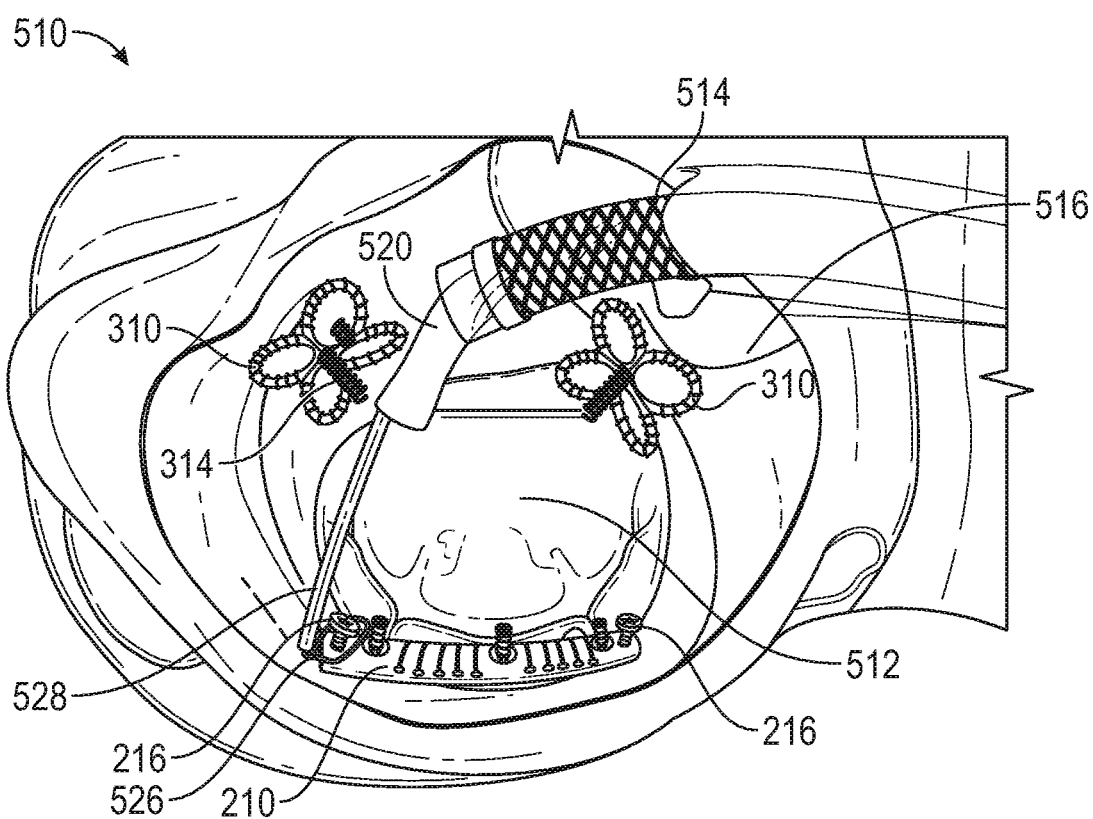
Figure 17:
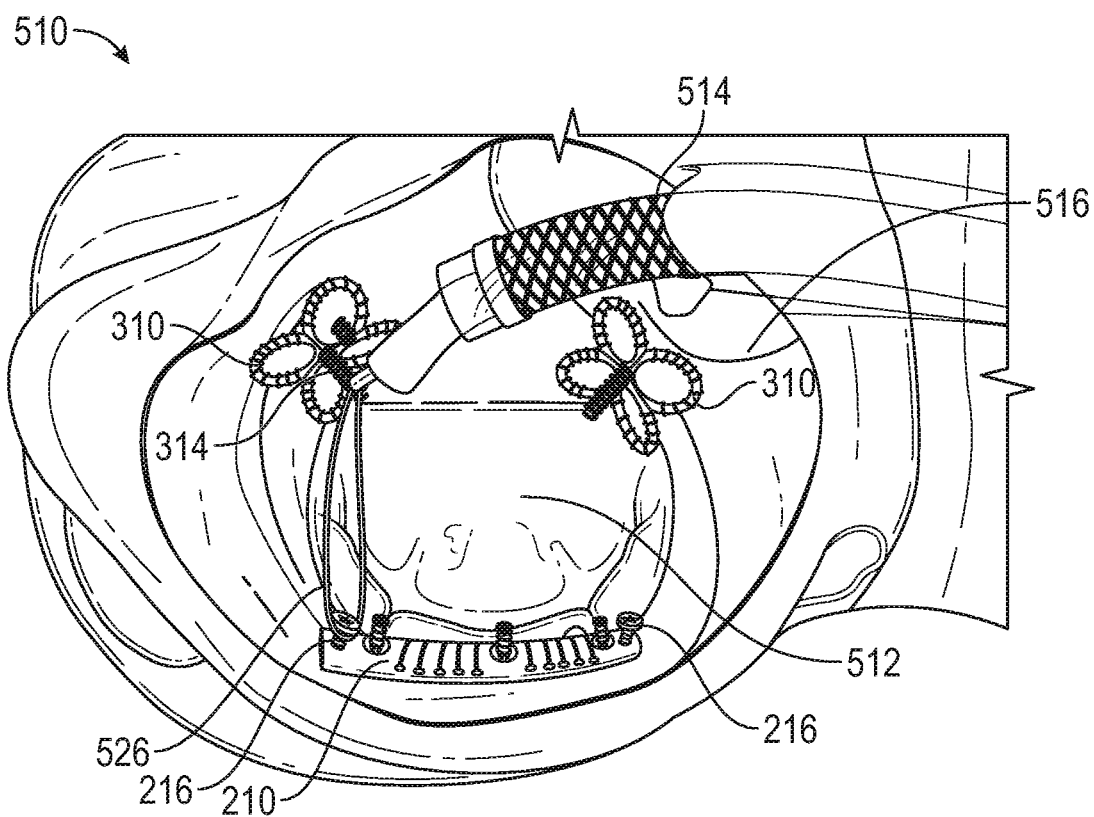
Figure 18:
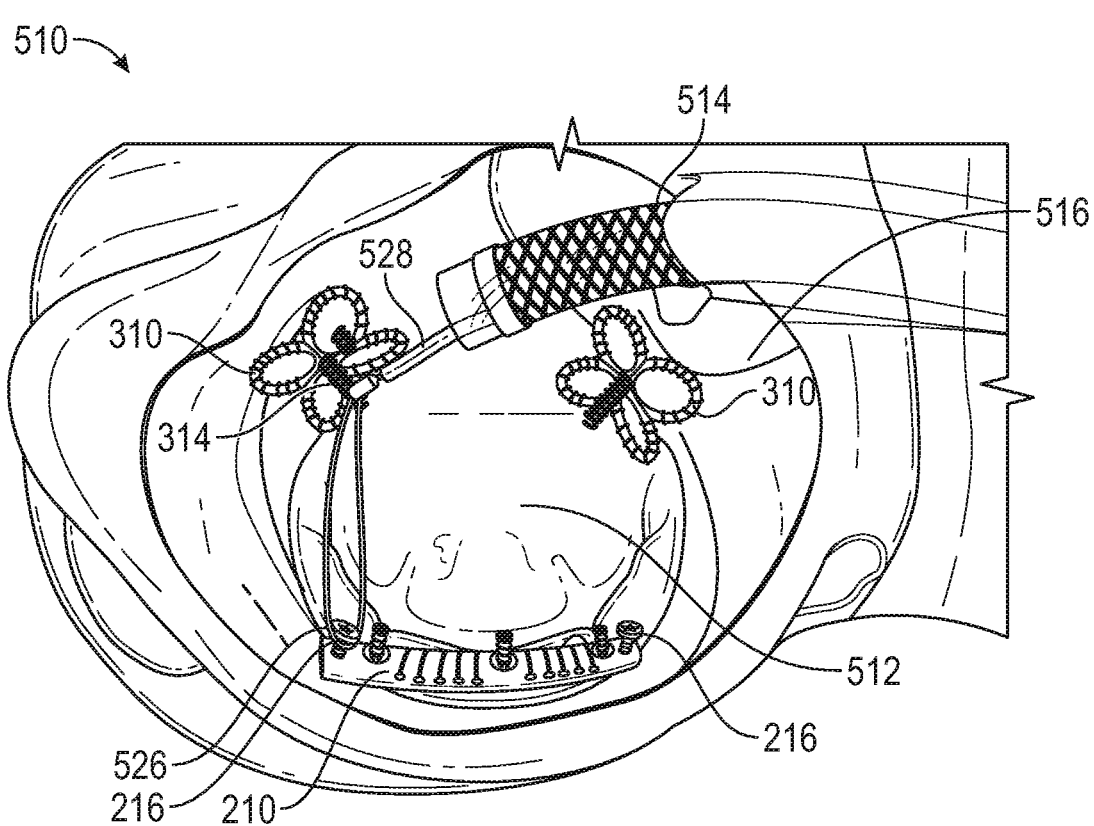

Referring to FIGS. 4 and 16-18, step 428 of exemplary method 410 will be described. In this step, first tensile member or snare 526 is attached to the posterior bar 210 (i.e. the first member) and anterior pad 310 (i.e. the second member.) Steerable inner catheter 520 and snare sheath 528 may be utilized to guide first tensile member 526 over the lateral snare feature 216 of bar 210, as shown in FIG. 16. First tensile member 526 may then be guided over primary tissue anchor 314 of anterior pad 310, as shown in FIG. 17. A small amount of tension may then be applied to first tensile member 526 with snare sheath 528 to keep it engaged with bar 210 and pad 310, as shown in FIG. 18.

Figure 19:
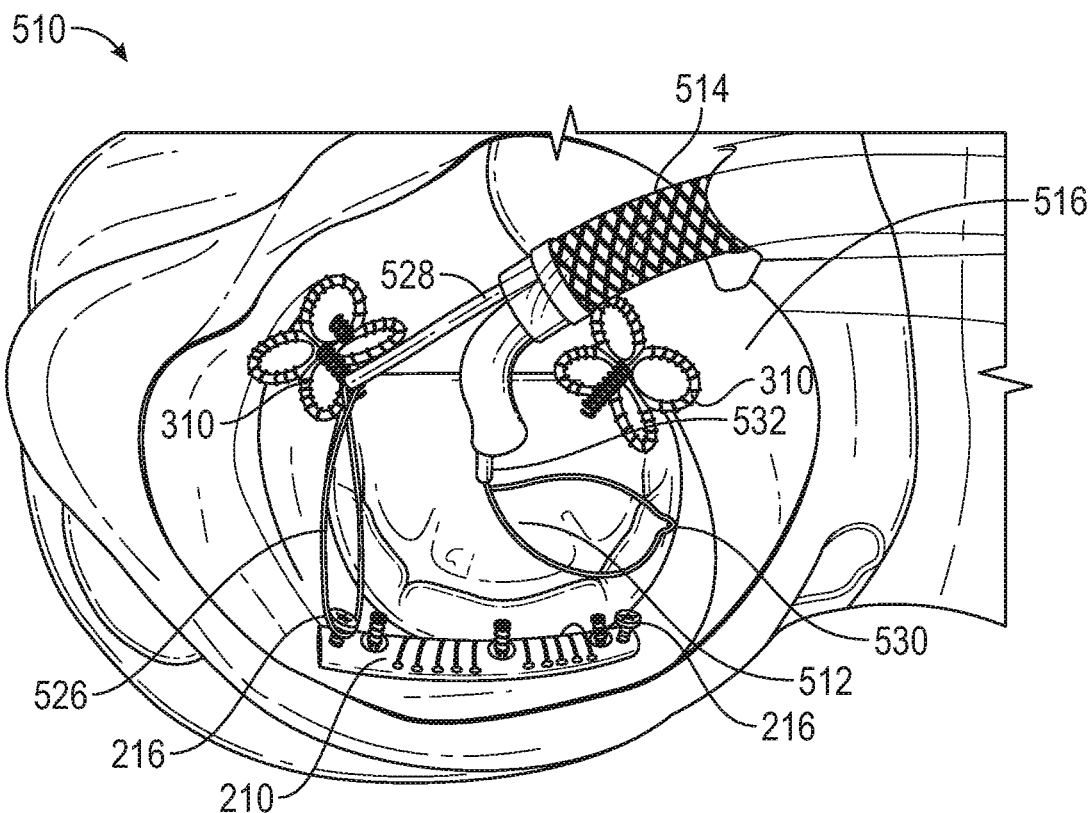

Referring to FIGS. 4 and 19, step 430 of exemplary method 410 will be described. In this step, a second tensile member or snare 530 is deployed from the distal end of catheter 514 through steerable inner catheter 520 as shown. A snare sheath 532 may be used to direct the second tensile member 530 toward implant features. Snare sheath 532 may also be used to tighten second tensile member 530 around the implant features by pulling proximally on the tensile member 530 relative to the sheath 532.

Figure 20:
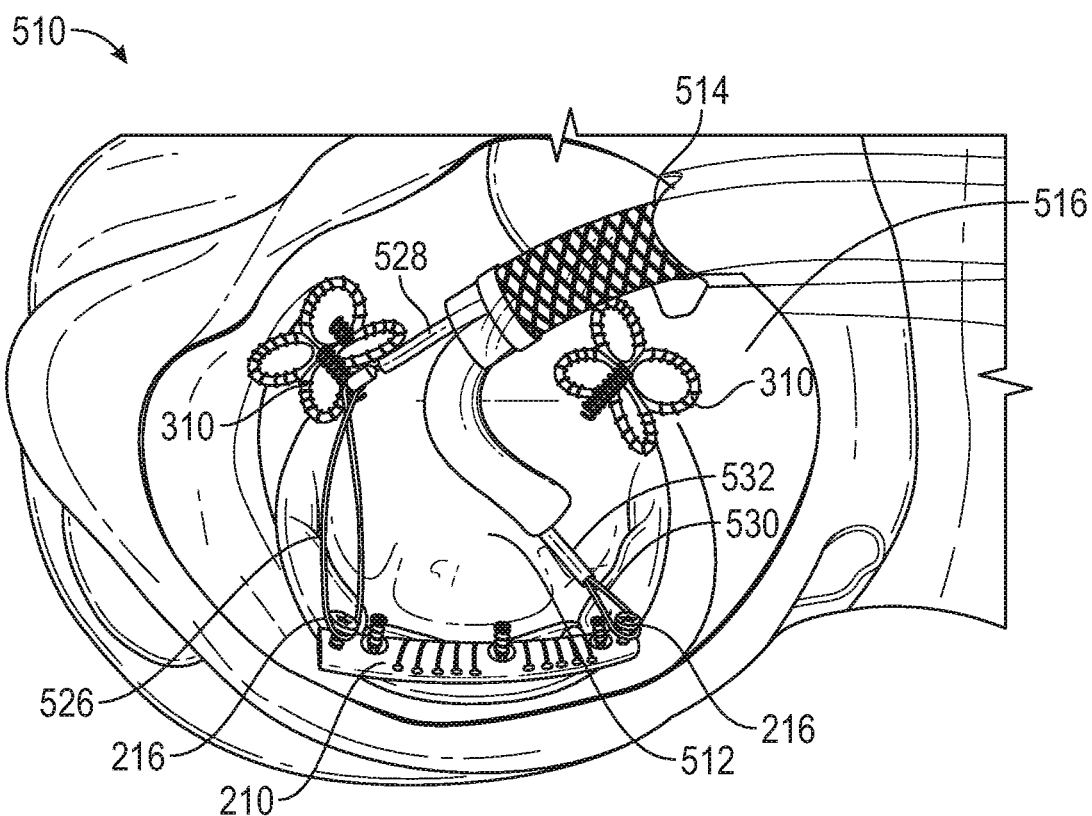
Figure 21:
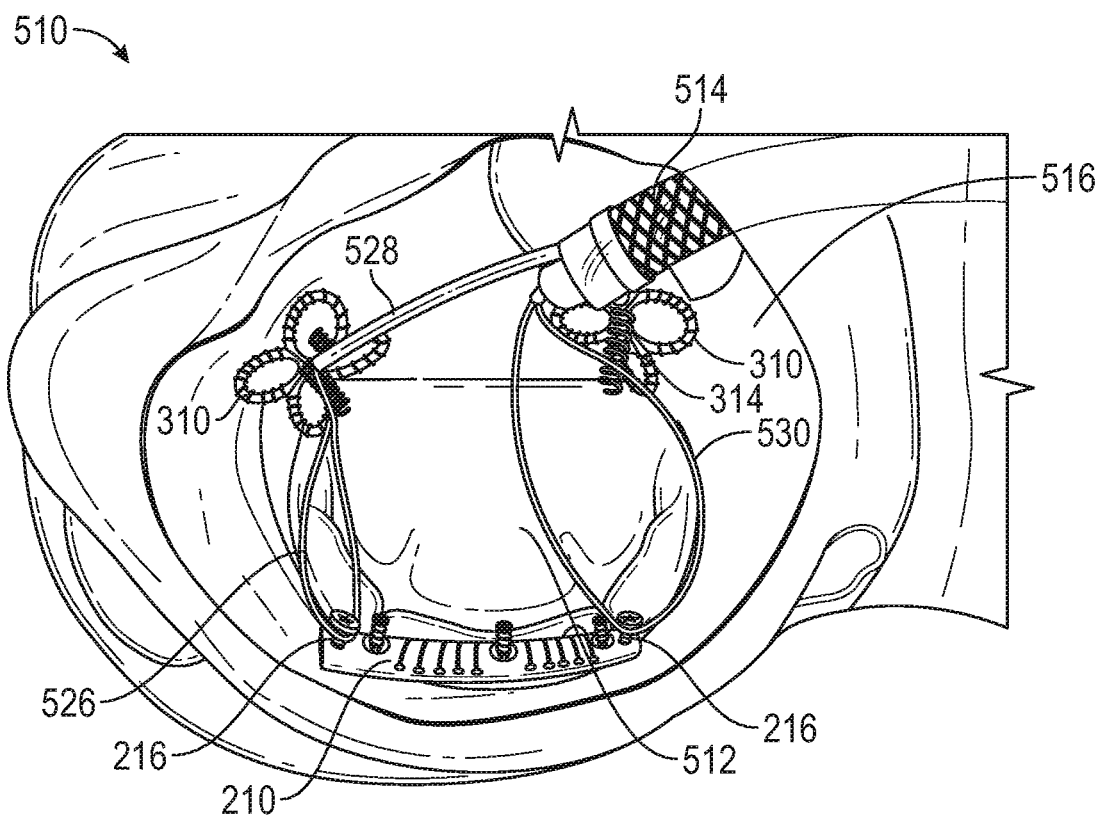
Figure 22:
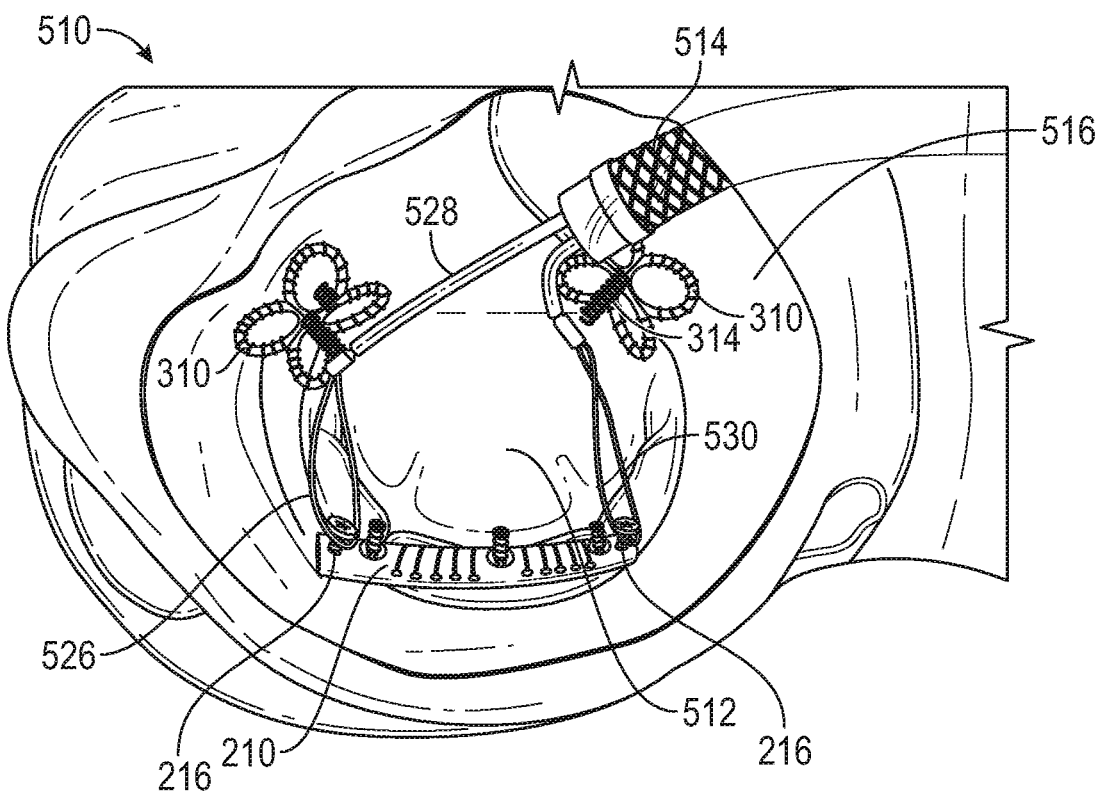
Figure 54:
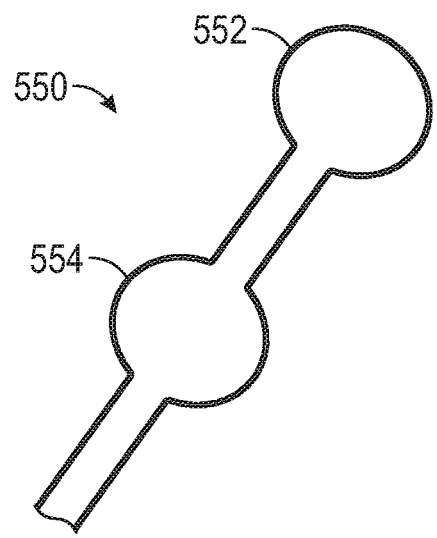
FIGS. 54-55 are top plan views showing additional examples of tensile member snares.
Figure 55:
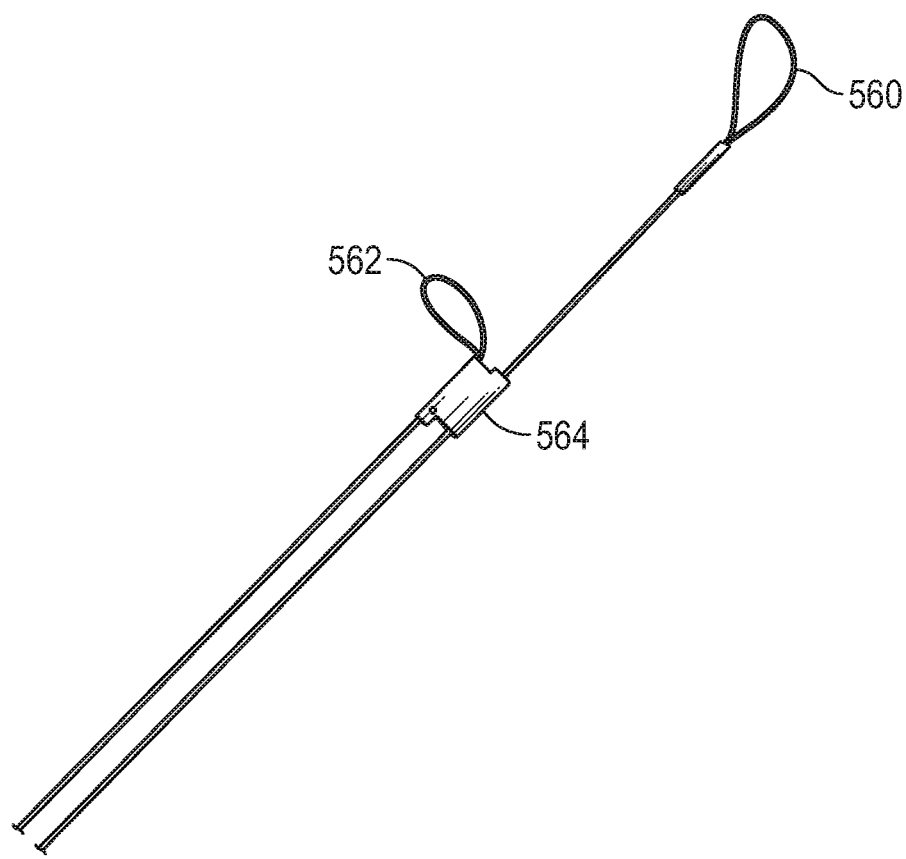

Referring to FIGS. 4 and 20-22, step 432 of exemplary method 410 will be described. In this step, second tensile member or snare 530 is attached to the posterior bar 210 (i.e. the first member) and the next anterior pad 310 (i.e. the third member.) Steerable inner catheter 520 and snare sheath 532 may be utilized to guide second tensile member 530 over the medial snare feature 216 of bar 210, as shown in FIG. 20. Second tensile member 530 may then be guided over primary tissue anchor 314 of anterior pad 310, as shown in FIG. 21. A small amount of tension may then be applied to second tensile member 530 with snare sheath 532 to keep it engaged with bar 210 and pad 310, as shown in FIG. 22. In some implementations, the snare shape may be configured to more easily engage the snare features on the implants. For example, each snare may form a D-shape that makes contact with the lateral side or medial side of the atrium. The wall of the atrium is then used to guide the snare down to the annulus and then cinch without necessarily needing to guide the snare to each snare feature. In some embodiments, the snare has a dumbbell (or dog bone) shape, such as the exemplary snare 550 shown in FIG. 54. Snare 550 includes a distal loop 552 and a proximal loop 554 having predefined diameter(s), with the rest of the snare having generally parallel tensile members forming a smaller gap between them than the loop diameter(s). Distal loop 552 may first be exposed to engage a first snare feature on an implant, and subsequently the proximal loop 554 may be exposed to capture a second snare feature on an implant. In some embodiments, as depicted in FIG. 55, two snares 560 and 562 are loaded in parallel, each with a predefined shape. Individual snares 560 and 562 may be connected with a coupler 564 and can slide independently to engage snare features on implants separately.

Once both first tensile member 526 and second tensile member 530 are in place, additional tension may be applied to both to draw the anterior and posterior sides of mitral valve 512 into closer approximation. In some implementations, tension in members 526 and 530 may be increased simultaneously. In some implementations, tension may be increased incrementally in members 526 and 530, alternating between the two until the desired tensions and or valve approximation is reached. In some implementations, the final tension and or tissue approximation of each tensile member 526 and 530 is approximately the same. In some implementations, the final tension and or tissue approximation of each tensile member 526 and 530 is different. Because medial and lateral cinching can be performed independently, the placement of each bar is more forgiving. This generally holds true for all of the systems disclosed herein. In some implementations, real time echocardiography of the mitral valve is used to monitor the reduction in mitral regurgitation as tensile members 526 and 530 are tightened.

After the desired tensions and or tissue approximations are obtained, tensile members 526 and 530 may be tied off. In some implementations, a reversible lock may be used during the cinching process which is configured to permanently hold the position of the tensile member. A disconnect member may be used to decouple the snare from the delivery system, or a portion of the tensile member may be cut to release it. Catheter 514 may then be withdrawn from the left atrium, along with steerable inner catheter 520 and snare sheaths 528 and 532 (step 436 shown in FIG. 4.) In addition to tensioning the device during the de novo procedure, additional tensioning devices can be added at a later time or date, and or the existing devices can be re-tensioned to further reduce the A-P dimension.

Figure 23:
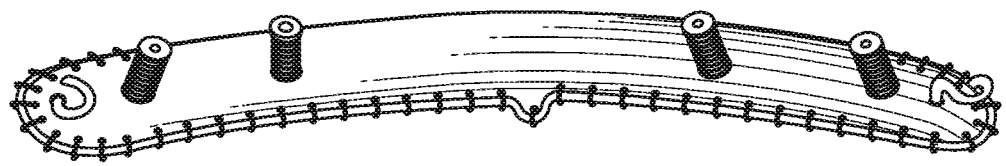
FIGS. 23-33B are perspective views showing additional examples of posterior bars and snare features.

Referring to FIGS. 23-33B, additional examples of posterior bars and snare features are provided. FIG. 23 shows a posterior bar similar to previously described bar 210 but having four tissue anchors and no center anchor. Additionally, snare features are provided on each end in the form of hooks.

Figure 24:
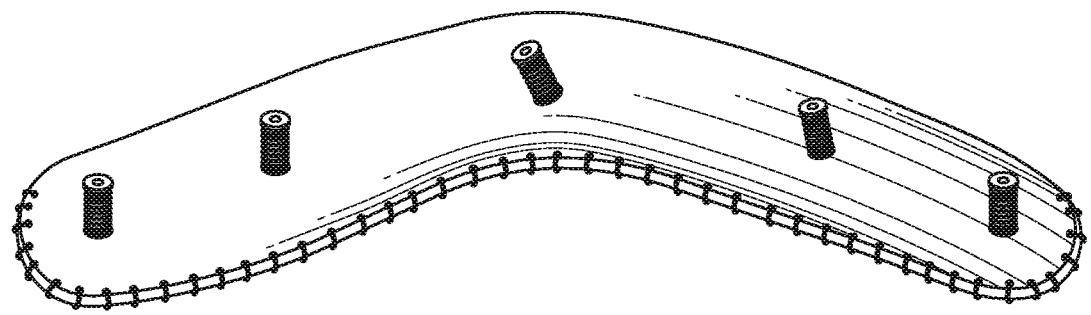

FIG. 24 shows a boomerang shaped posterior bar with five tissue anchors, the center anchor being larger than the other four and used for torque control of the implant. In this embodiment, the anchors may be used as snare features. In some embodiments (not shown), the bar shape has a compound radius of curvature that becomes tighter as the bar extends away from the posterior side to match the curvature of the valve annulus.

Figure 25:
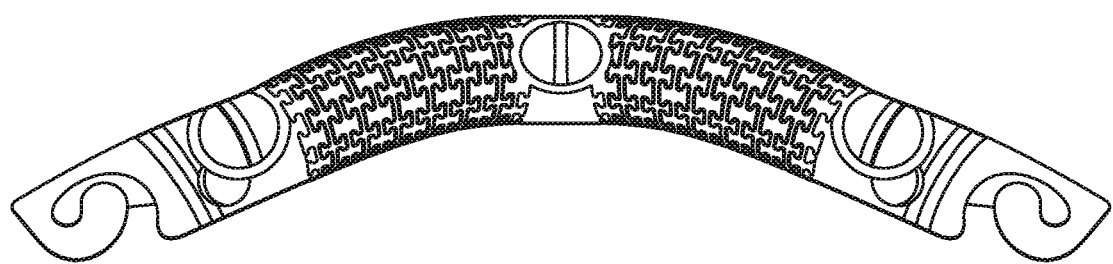

FIG. 25 shows a posterior bar with no fabric covering. Three apertures are provided with a transverse bar across each one for pivotably attaching tissue anchor guides, similar to those of posterior bar 210. A hook-shaped slot may be provided at each end as shown to capture the snares. The tube may be laser cut with interlocking features as shown to allow the bar to flex with limited amount of bend and elongation.

Figure 26:
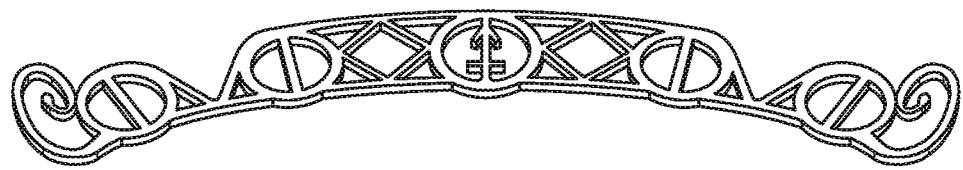

FIG. 26 shows a low-profile posterior bar formed from a laser cut sheet. This implant provides similar functionality to the bar of FIG. 23 and has a center torque control feature. A similar implant (not shown) may be formed from wire. Such an implant can be very robust, provide spring-like flexibility and can include more pronounced snare features.

Figure 27:
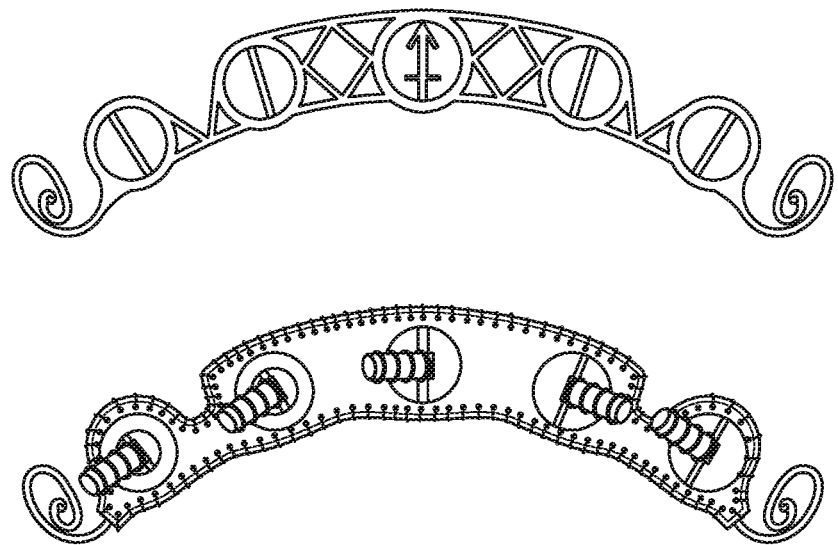

FIG. 27 shows an implant similar to the one shown in FIG. 26, both with and without a fabric covering.

Figure 28:
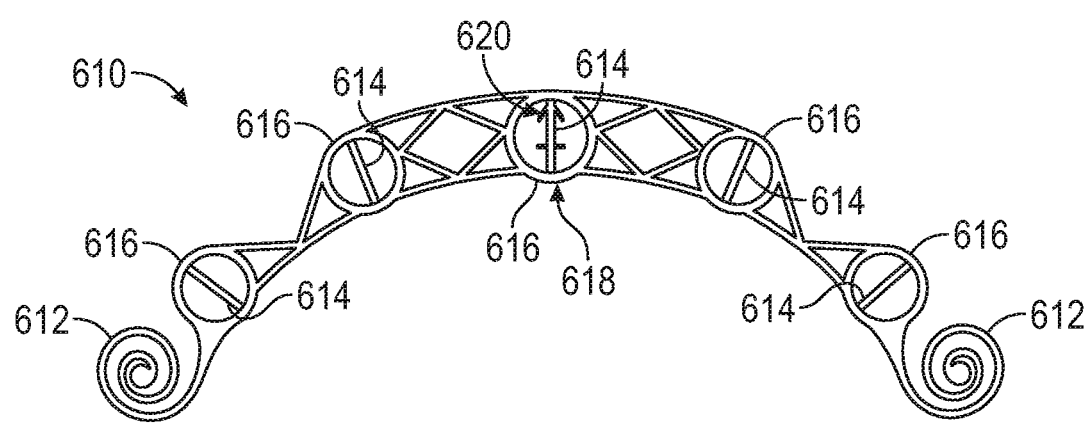

FIG. 28 shows another similar implant 610 with helical snare features 612 at both ends, lead nut tabs 614 in each of the five anchor locations 616, a torque control attachment 618, and a tab 620 configured to center the lead nut/anchor guide (not shown) in the middle anchor location. Helical snare features 612 can be raised with respect to the plane of posterior bar 610 to allow easier engagement with a tensile member. A tab at the end of the helix may be provided with enhanced visibility with fluoroscopy and echocardiography. The tab may be configured to help retain the tensile member.

Figure 29:
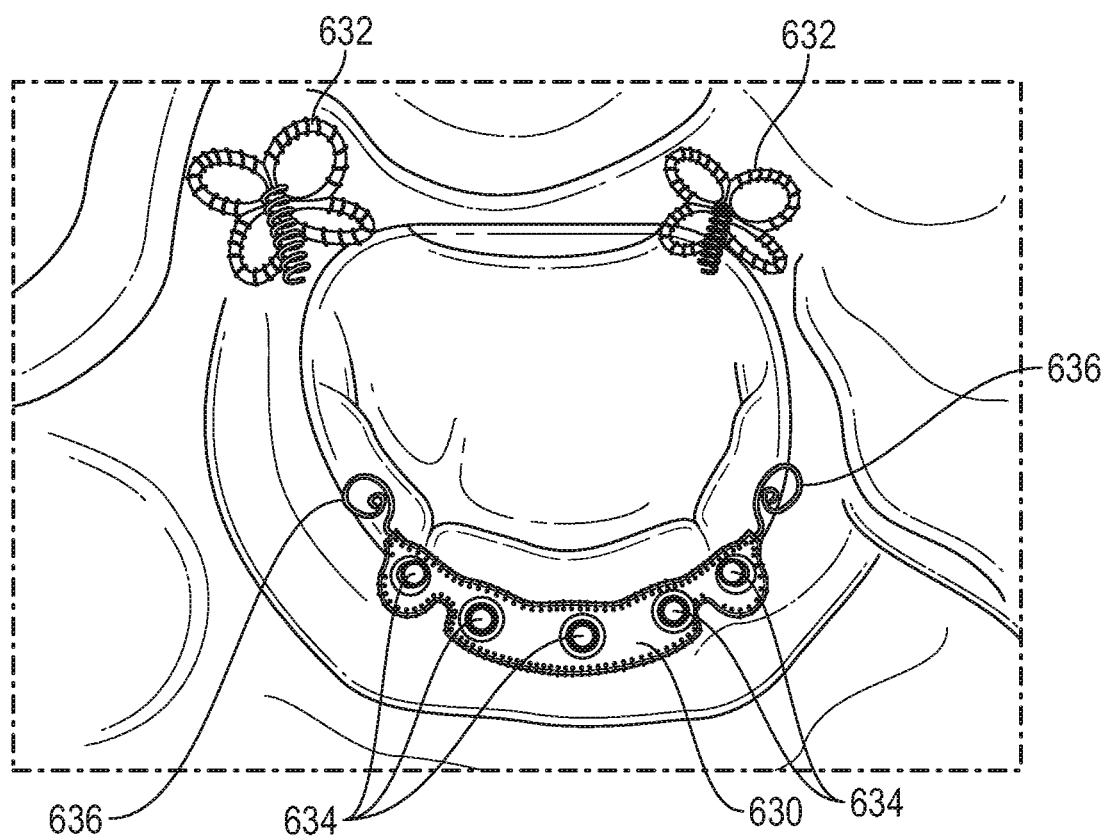

FIG. 29 shows a posterior bar 630 and two anterior pads 632 in an implanted configuration. Posterior bar 630 includes a fabric covering, five anchors 634 and two snare features 636 extending in a generally longitudinal direction from the fabric covering in opposite directions.

Figure 30:
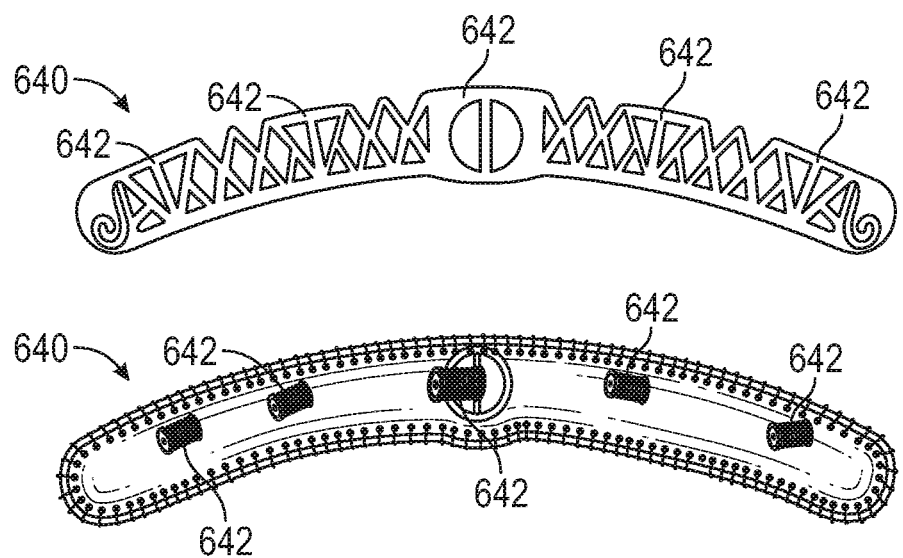

FIG. 30 shows two posterior bars 640, one with and one without a fabric covering. Bar 640 includes five anchor locations 642 and an overlapping triangle truss configuration.

Figure 31:
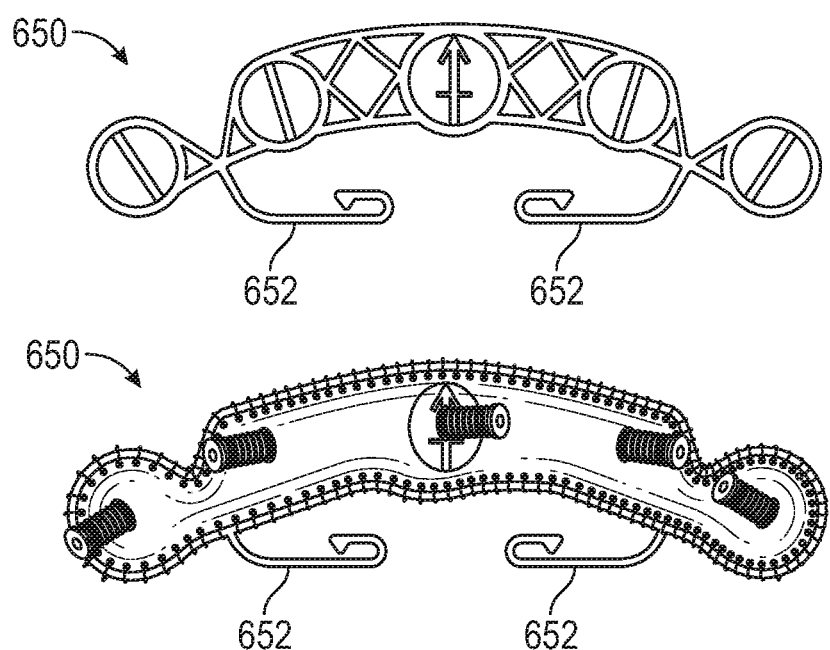

FIG. 31 shows two posterior bars 650, one with and one without a fabric covering. Bar 650 includes two snare features 652 that extend in a generally radially inward direction and towards one another.

Figure 32:
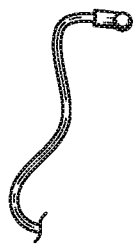
Figure 33A:
Figure 33B:

FIGS. 32, 33A and 33B show exemplary wire ends that may be used as snare features. In some embodiments, a ball at the end of the snare feature is configured for enhanced visibility with fluoroscopy and echocardiography. A gap between the ball end of the snare feature and the main body of the implant may be configured to allow the tensile member to slide onto the snare feature with a slight deflection of the snare feature. The snare feature then springs back to retain the tensile member on the snare feature.

In some embodiments, the posterior bars are curved to match the anatomy of the mitral annulus adjacent to the posterior leaflet. They may be configured to be low profile to minimize the amount of irregular structure in the atrium that might be a potential site for thrombosis.

Figure 34:
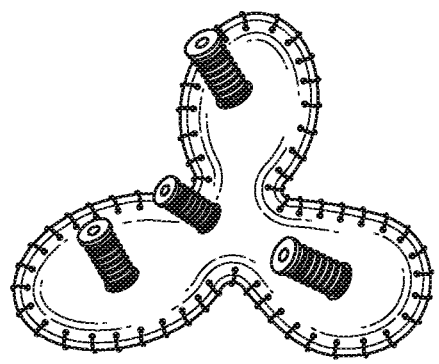
FIGS. 34-37 are perspective views showing additional examples of anterior pads.
Figure 35:
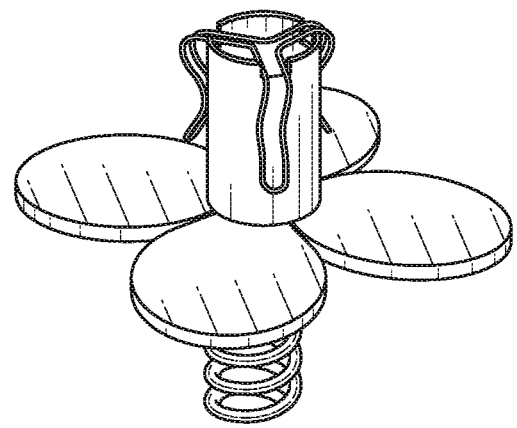
Figure 36:
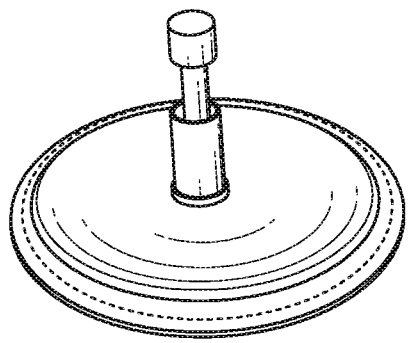
Figure 37:
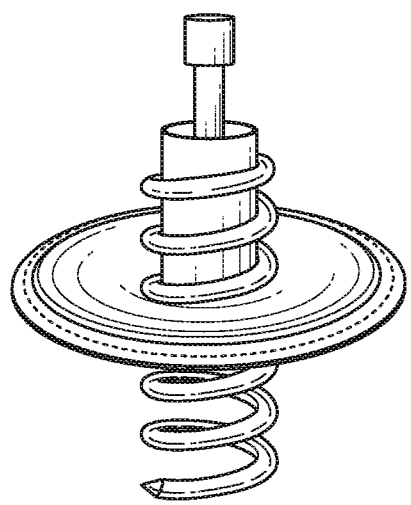

Referring to FIGS. 34-37, additional examples of anterior pads are provided. FIG. 34 shows an anterior pad similar to previously described pad 310 but having three petals. FIG. 35 shows an anterior pad having a center tower with three snare features attached. FIG. 36 shows a circular pad with no petals and a stepped snare feature. FIG. 37 shows a circular pad with no petals and a snare feature atop a protruding tissue anchor.

In some embodiments, the anterior pads allow for targeted additional anchoring after a primary anchor is placed. They can be low profile to minimize the amount of irregular structure in the atrium that might be a potential site for thrombosis. The pad edges can be configured to be atraumatic to limit the potential for tissue damage. In some embodiments, the anterior pads are covered in PET fabric to aid tissue ingrowth. The pads can be configured to preferentially load the anchors in shear rather than tension with respect to the anatomy. Prominent snare features can be provided to prevent snares from disengaging during implant manipulation. In some embodiments, the pads are configured to be easily imaged under fluoroscopy and echocardiography.

Figure 38:
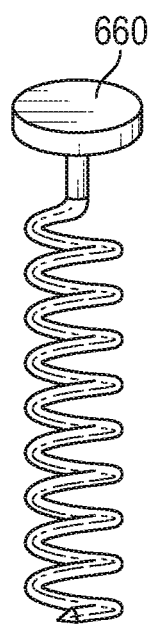
FIGS. 38-40 are side views showing additional examples of helical tissue anchors.
Figure 39:
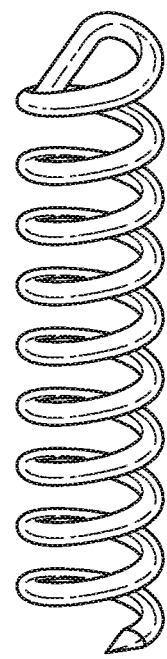
Figure 40:

In other embodiments (not shown), the positions of the bar and pads may be reversed such that a bar is placed on the anterior side of the mitral annulus and two pads are placed on the posterior side. In some embodiments, the posterior element can be two separate pieces, one on the lateral side and one on the medial side, such that there are four pads around the valve and no bar. In some embodiments, a single snare or tensile member may be used to connect and adjust all of the implanted components. Also, individual snares can be used to independently engage each snare feature and the two snares on each side can be tensioned together (i.e. four snares total). Additionally, a separate tensioning member can be placed between the two trigone pads for further tissue stabilization and full circumferential engagement. Such a system, or any of the systems disclosed herein, may be used as an anchoring system for a valve replacement Referring to FIGS. 38-40, additional examples of helical tissue anchors are provided. FIG. 38 shows an anchor having a straight, gap-free interface feature located at its top. This feature allows the anchor to spin freely in the implant at the end of travel when being inserted to eliminate any gaps between the implant and the tissue. An implant retention tab 660 may be located at the top of the straight section such that the coil can continue to drive into the tissue while the straight section spins freely in the implant until the implant is brought into close contact with the tissue. FIG. 39 shows an anchor with a low profile head. An anchor having a low profile minimizes the amount of irregular structure in the atrium that might be a potential site for thrombosis. FIG. 40 shows a pair of anchors, each with a head attached for driving the anchor. In some embodiments, the anchors are configured to provide strong attachment strength to tissue, be retrieved if necessary, and be easily imaged under fluoroscopy and echocardiography.

Figure 41:
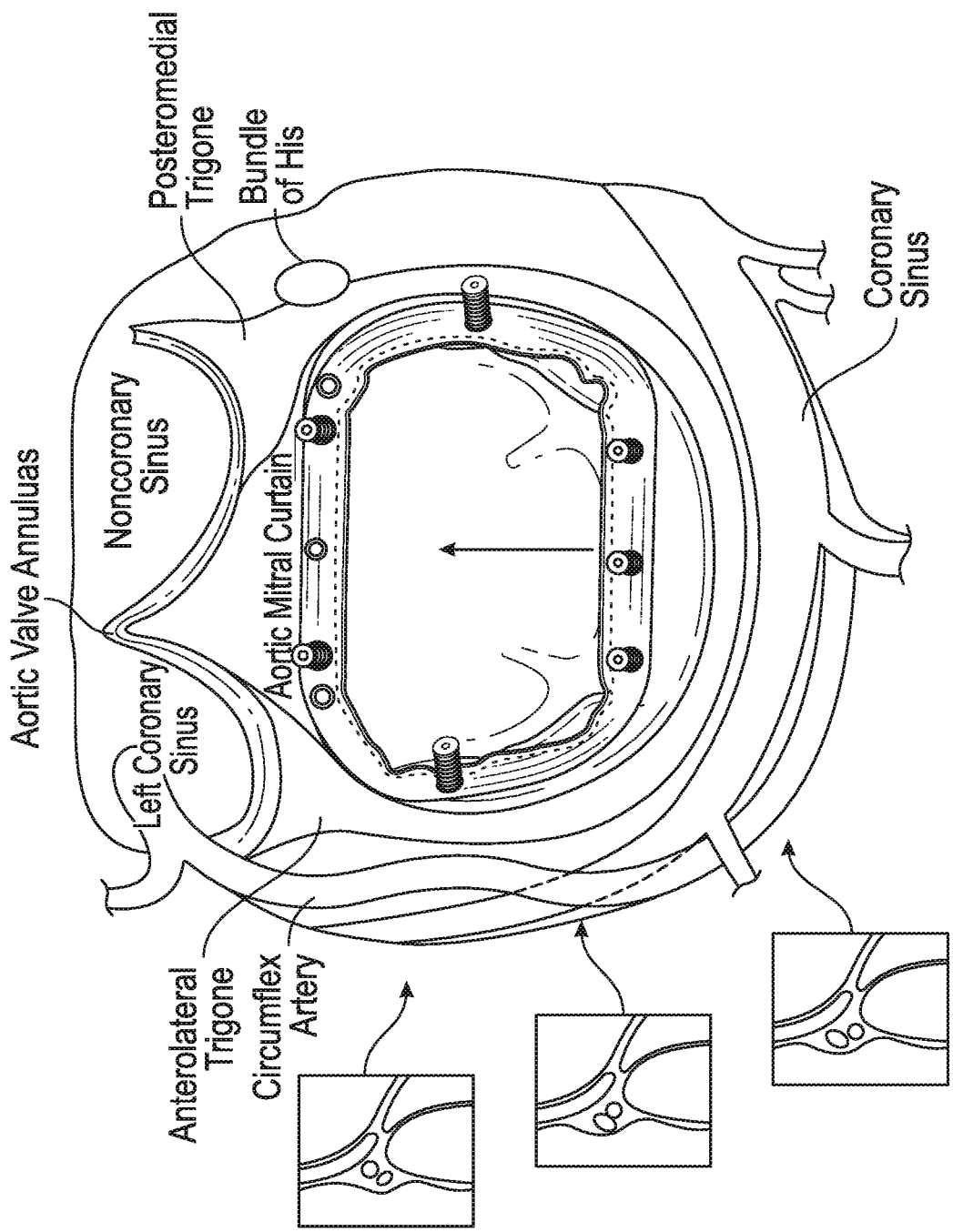
FIGS. 41-44 are top plan views showing further exemplary embodiments of annuloplasty systems constructed according to aspects of the present disclosure.
Figure 42:
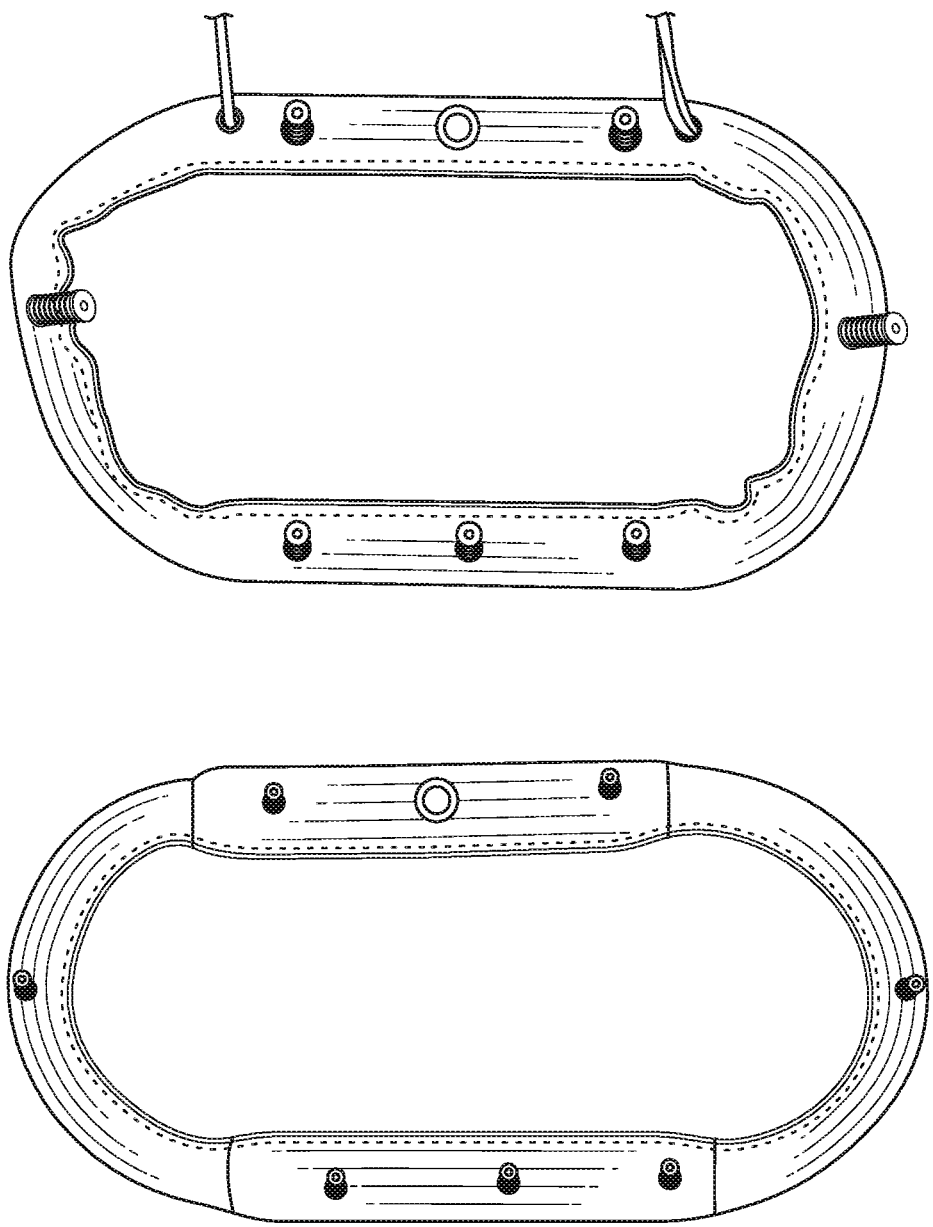
Figure 43:
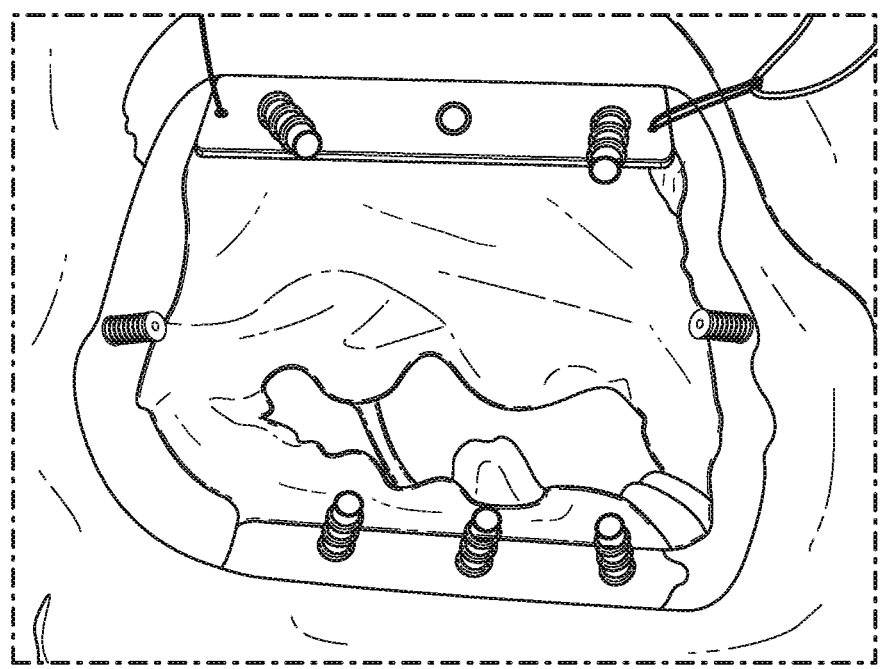
Figure 44:
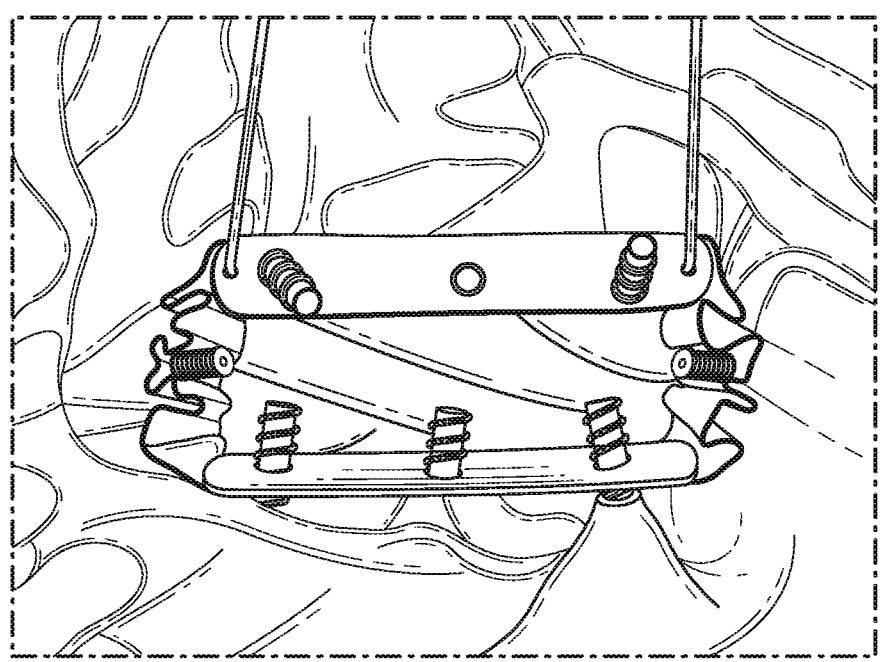

Referring to FIGS. 41-44, further exemplary embodiments constructed according to aspects of the present disclosure are shown. In these embodiments, two structures or "bars" are placed on opposite sides of the mitral annulus, one on the posterior side and the other on the anterior side. The two medial ends of each bar are connected together and the two lateral ends are connected. Each side may then be brought into closer approximation to reduce the A-P dimension of the valve. This focuses the annular change in the A-P direction. The cinching mechanisms may be covered with PET material as shown, which can form pleats as the implant is tightened. The connection of the two bars creates a full "ring" structure. The posterior bar may be curved to match the shape of the annulus, as shown in FIG. 41. The anterior bar may be straighter to bridge between the lateral and medial trigones. Because medial and lateral cinching can be performed independently, the placement of each bar is more forgiving. Again, this generally holds true for all of the systems disclosed herein. As shown in FIGS. 42-44, one or more anchors may be placed on the side portions of the ring.

Figure 45:
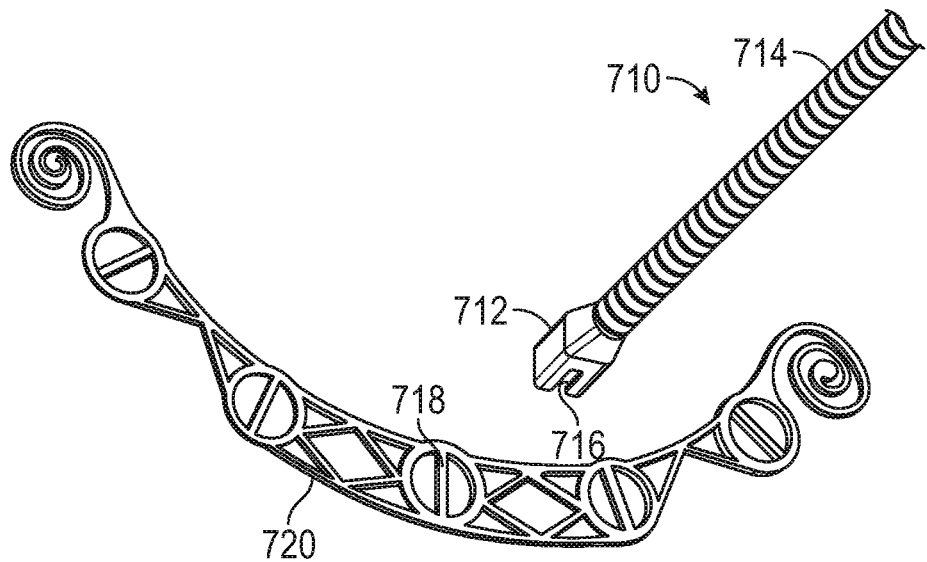
FIGS. 45-51 are perspective views showing an exemplary embodiment of torque control of a posterior bar.
Figure 46:
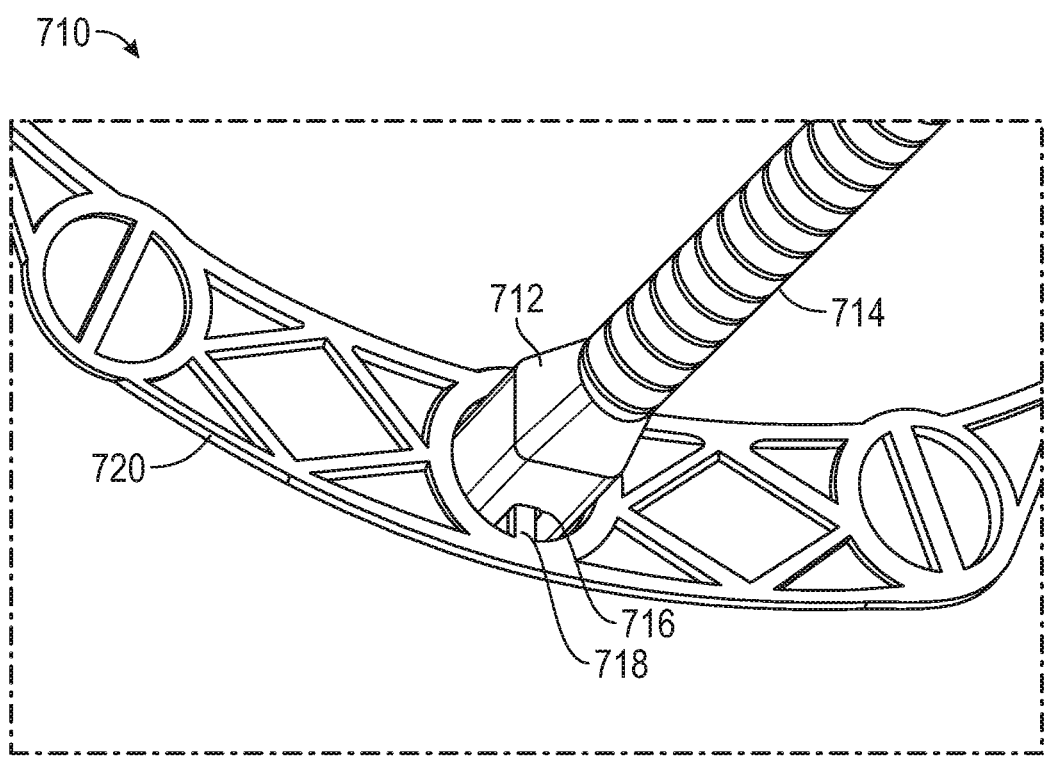
Figure 47:
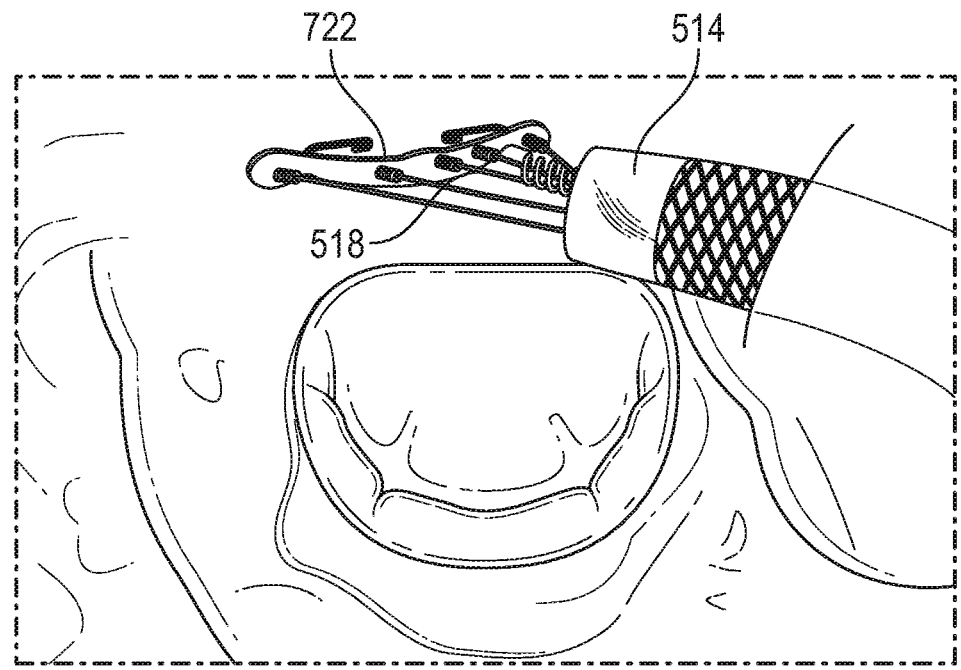
Figure 48:
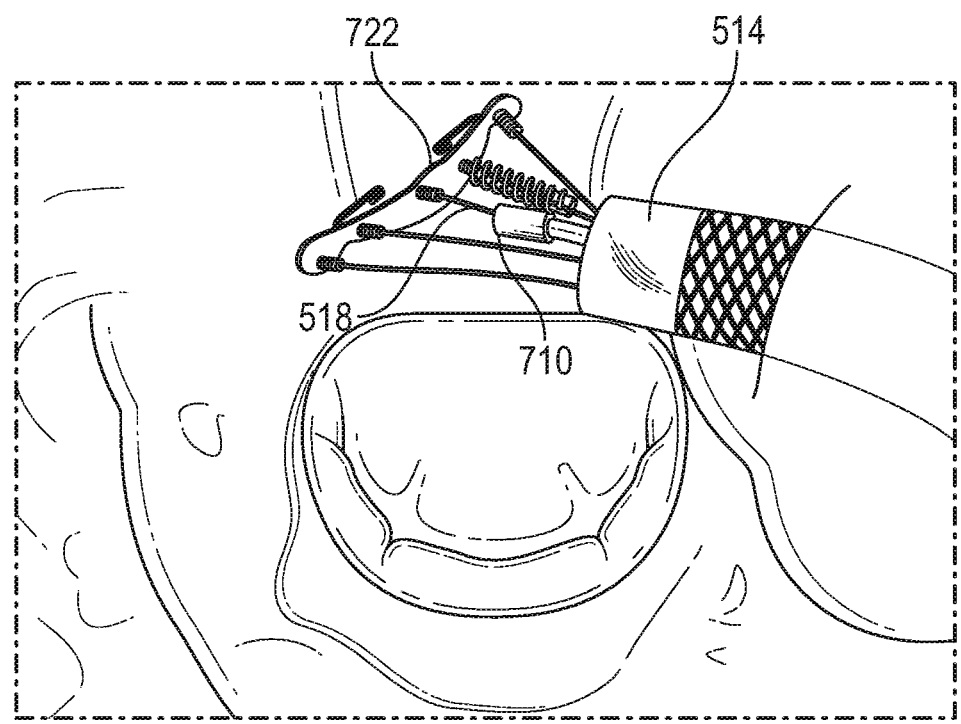
Figure 49:
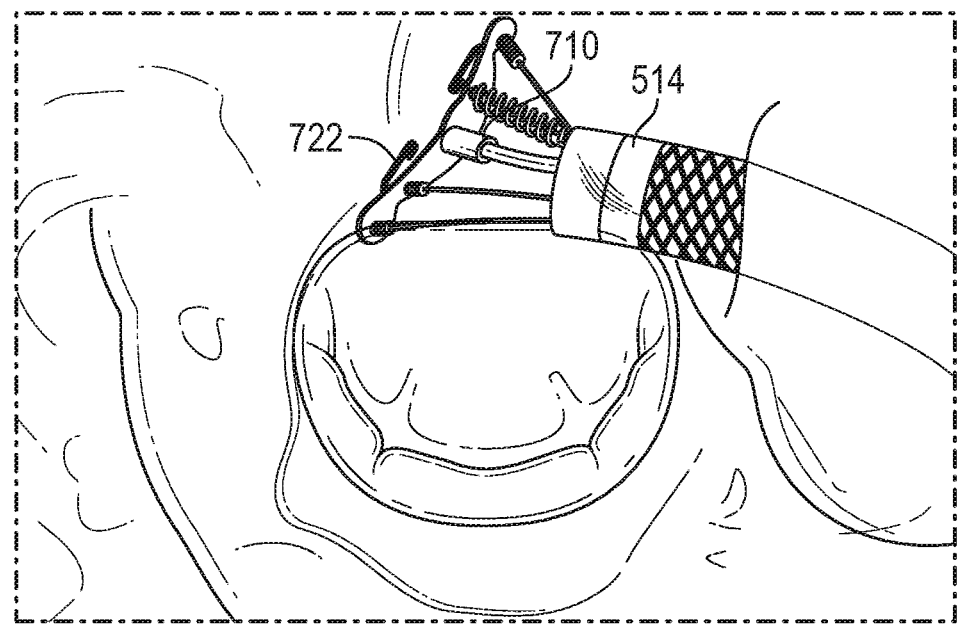
Figure 50:
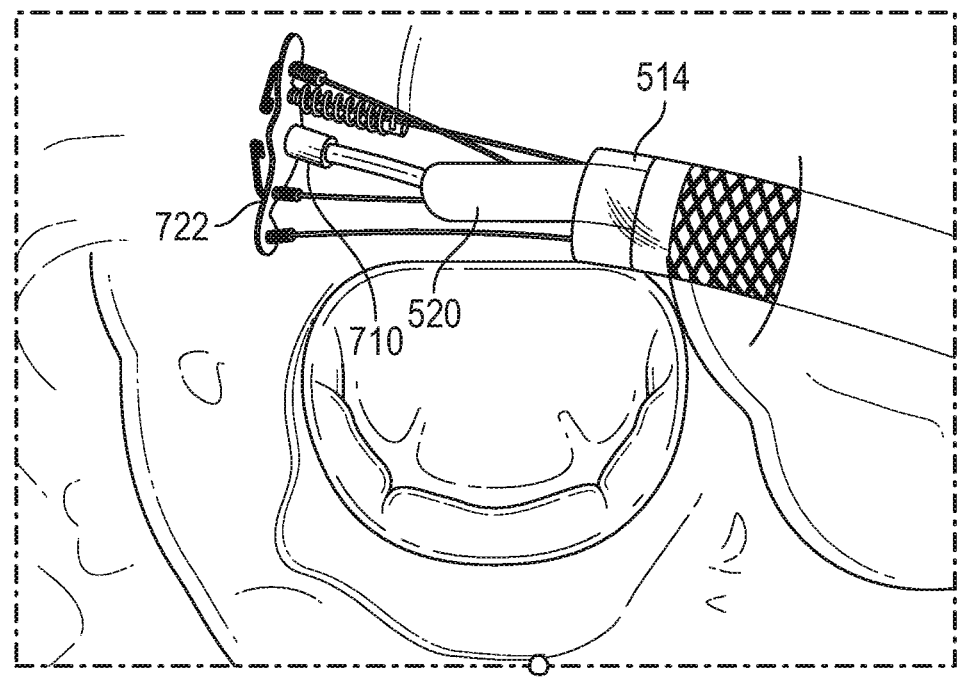

Referring to FIGS. 45-51, an exemplary embodiment of torque control of a posterior bar will be described. In this embodiment, a torque driver 710 is provided. Torque driver 710 includes a head 712 located on its distal end, and a flexible shaft 714 attached to the head and whose proximal end extends outside the patient's body such that head 712 can be manipulated by a surgeon. As best seen in FIGS. 48 and 50, when in use, torque driver 710 resides coaxially between the center lead 518 and the steerable catheter 520. As best seen in FIG. 45, the head 712 includes a transverse slot 716 configured to engage with center tab 718 of posterior bar 720. As best seen in FIG. 46, when torque driver 710 is rotationally aligned and pushed distally against posterior bar 720, slot 716 engages with tab 718 to allow torque driver 710 to accurately control the rotational orientation of posterior bar 720 even when rotational resistance is encountered. (For clarity, posterior bar 720 is shown in FIGS. 45 and 46 without a fabric cover, lead nuts, leads, etc.)

In some embodiments, head 712 has a square cross-sectional shape, as shown. In other embodiments (not shown), the torque driver head may have a circular or other cross-sectional shape. In some embodiments, the outer dimensions of head 712 fit closely within mating features on posterior bar 720 (such as the ring shown in FIG. 46) to constrain the lateral movement of head 712 relative to bar 720. In other embodiments (not shown), other centering features may be provided to limit lateral movement.

Figure 51:
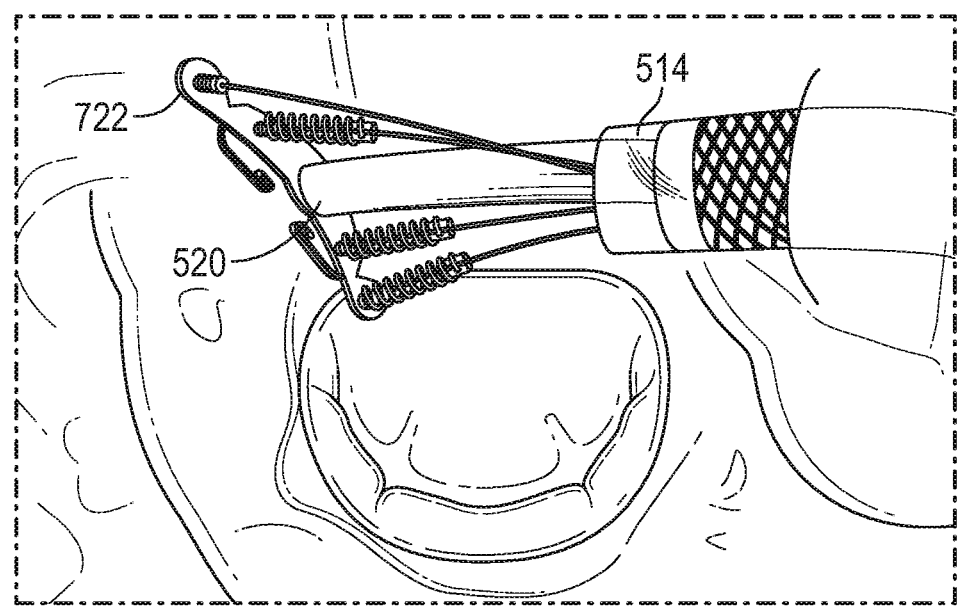

FIGS. 47-51 illustrate an exemplary method of use of torque driver 710. FIG. 47 shows posterior bar 722 being deployed from outer guide or catheter 514. FIG. 48 shows torque driver 710 being advanced through inner steerable sheath 520 (not seen in FIG. 48) and over center lead 518. FIG. 49 shows torque driver 710 engaging with posterior bar 722, as previously described. In some implementations, the surgeon pulls back and applies tension on center lead 518 while holding torque driver 710 in place. Once torque driver 710 engages with the center of bar 722, the position of torque driver 710 may be locked on the back (proximal) end of the inner steerable catheter 520. In FIG. 50, torque driver 710 is now positively locked to bar 722. Inner steerable catheter 520 is shown being advanced from outer guide 514. FIG. 51 shows inner steerable catheter 520 being advanced until it covers the torque driver and reaches bar 722. Posterior bar 722 is now ready to be steered into place using torque driver 710 and or steerable catheter 520.

Figure 52:
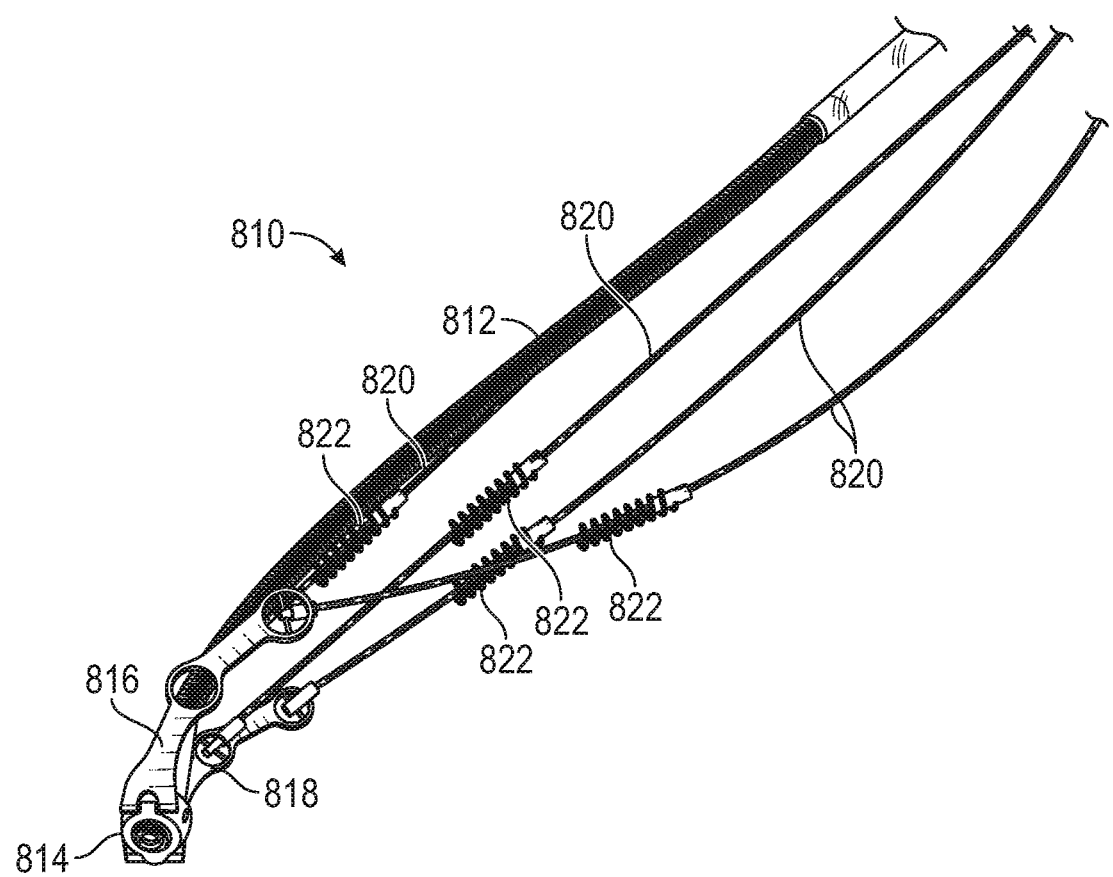
FIGS. 52-53 are perspective views showing an exemplary embodiment of a foldable implant.
Figure 53:
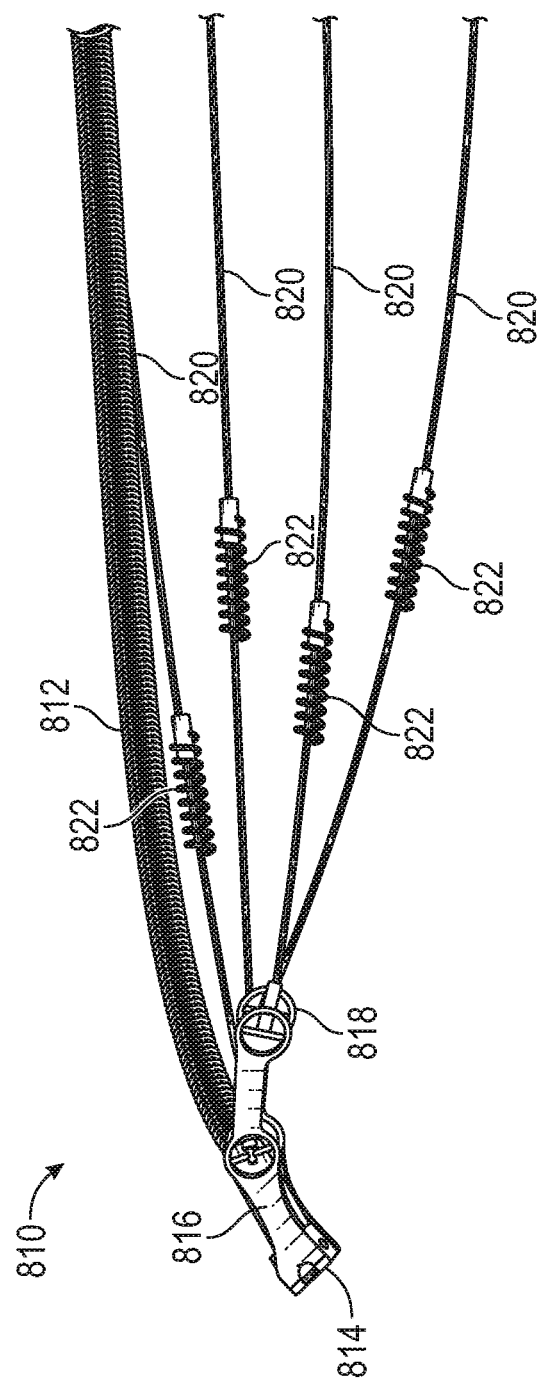

Referring to FIGS. 52 and 53, another exemplary embodiment is shown wherein a foldable posterior bar is provided. Foldable bar 810 may be configured to aid in loading the device into a catheter (not shown) and for ease of manipulation in the left atrium. In this exemplary embodiment, posterior bar 810 includes three discrete sections: a center section 814, a right section 816 and a left section 818. Right section 816 and left section 818 are each hingedly connected to opposite sides of center section 814, as shown. In this embodiment, right section 816 and left section 818 may each rotate between a retracted position (as shown) to an extended position (not shown) in which they are each generally coplanar with center section 814. One or more leads 820 may be coupled with each of the right section 816 and left section 818 to aid in unfolding each section. Each section 816 and 818 may rotate through about 90 degrees when traveling between the retracted position and the extended position. In some embodiments, the right 816 and left 818 sections can be configured to lock in an open position once extended. In other embodiments (not shown), only two sections, or more than three sections that fold relative to one another may be provided.

Similar to previously described embodiments, posterior bar 810 may be provided with five anchors 822, with one anchor for center section 814, two anchors for right section 816 and two anchors for left section 818. In some implementations, the center anchor may be placed first (with the side sections 816 and or 818 retracted or extended), and in other implementations a side anchor may be placed first. As with previously described embodiments, a torque driver, a steerable sheath 812, or a combination thereof may be provided to aid in maneuvering the device to the desired implantation site.

In some embodiments, the systems and methods disclosed herein or portions thereof may be utilized in a similar manner on either atrioventricular valve.

Advantages provided by the systems and methods disclosed herein can include the following. A more direct reduction in the anterior-posterior (A-P) direction can be achieved. This can be accomplished with a reduced cinching force because the action is directly in the A-P direction, rather than larger forces that are generally needed with circumferential remodeling. Lower cinching force typically translates to fewer anchors required. The systems and methods also allow for a high level of customization to suit a particular anatomy. This relates to there being distinct components that are placed separately, and the ability to adjust the medial and lateral sides separately. The separate components are each easier to implant compared with one superstructure. The systems and methods allow for in vivo adjustability, allow for reduced accuracy needed to place the components and simplify the implantation procedure. A smaller number of implant sizes and configurations can also be accommodated. In addition to tensioning the device during the de novo procedure, additional tensioning devices can be added at a later time or date, and or the existing devices can be re-tensioned to further reduce the A-P dimension.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about", "approximately" or "generally" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implantable annuloplasty system comprising:
   a first member;
   at least one first member anchor configured to anchor the first member to an anterior side of a mitral valve annulus in a left atrium of a heart;
   a second member that is separate from the first member and is configured to not directly contact the first member;
   at least one second member anchor configured to anchor the second member to a posterior side of the mitral valve annulus in the left atrium;
   a third member that is separate from the first member and the second member and is configured to not directly contact the first member or the second member;
   at least one third member anchor configured to anchor the third member to the anterior side of the mitral valve annulus in the left atrium;
   a first flexible tensile member configured to span directly between the first member and the second member in a first straight line such that tension may be applied to the first tensile member to draw the first member and the second member toward one another and bring the posterior side and the anterior side of the mitral valve annulus into closer approximation; and
   a second flexible tensile member configured to span directly between the second member and the third member in a second straight line such that tension may be applied to the second tensile member independently from the tension applied to the first tensile member to draw the second member and the third member toward one another and bring the posterior side and the anterior side of the mitral valve annulus into closer approximation,
   wherein all elements of the implantable annuloplasty system are configured to be deployed into the left atrium through a catheter.

2. The annuloplasty system of claim 1, wherein the second member is elongated.

3. The annuloplasty system of claim 2, wherein the second member comprises a series of slits that allows the second member to flex.

4. The annuloplasty system of claim 2, wherein the second member is capable of taking on a curved shape.

5. The annuloplasty system of claim 1, wherein the second member comprises at least two extended features, each configured to engage either the first tensile member or the second tensile member.

6. The annuloplasty system of claim 5, wherein the second member is elongated and the at least two extended features are located on opposite ends of the second member.

7. The annuloplasty system of claim 1, further comprising an anchor guide mounted to the second member and configured to guide the at least one second member anchor into heart tissue.

8. The annuloplasty system of claim 7, wherein the anchor guide is configured to guide the at least one second member anchor in a generally perpendicular manner relative to the second member in an anterior-posterior direction.

9. The annuloplasty system of claim 7, wherein the anchor guide comprises a lead that extends proximally from the anchor guide and through the catheter to a proximal end of the catheter, wherein the lead is configured to guide the at least one second member anchor distally from the catheter to the anchor guide.

10. The annuloplasty system of claim 7, wherein the anchor guide is foldable relative to the second member, thereby allowing the anchor guide to generally lie flat against the second member when loading the second member and the anchor guide into the catheter.

11. The annuloplasty system of claim 1, wherein the second member comprises at least one hinge, thereby enabling the second member to be foldable along at least one discrete hinge axis.

12. The annuloplasty system of claim 1, further comprising at least one lead attached to each of the first member, the second member and the third member.

13. The annuloplasty system of claim 1, wherein the first tensile member is attached to the first member.

14. The annuloplasty system of claim 1, wherein the first tensile member is attached to the first member and the second tensile member is attached to the third member.

15. The annuloplasty system of claim 1, wherein the first member and the third member do not have a tensile member spanning between them.

16. The annuloplasty system of claim 1, wherein the first tensile member does not directly contact the second tensile member.

17. The annuloplasty system of claim 1, wherein at least a portion of the first flexible tensile member and at least a portion of the second flexible tensile member each is configured to pass directly over a mitral valve opening.

* * * * *